(12) United States Patent
Mori et al.

(10) Patent No.: US 6,909,793 B1
(45) Date of Patent: Jun. 21, 2005

(54) DATA INPUT APPARATUS, DATA INPUT SYSTEM, DISPLAYED DATA ANALYZING APPARATUS AND MEDIUM

(75) Inventors: Yasuhiro Mori, Izumi (JP); Masaki Yamauchi, Kadoma (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 562 days.

(21) Appl. No.: 09/656,316

(22) Filed: Sep. 6, 2000

(30) Foreign Application Priority Data

Sep. 9, 1999 (JP) .......................................... 11-256330
Dec. 7, 1999 (JP) .......................................... 11-348101

(51) Int. Cl.$^7$ ............................................... G06K 9/00
(52) U.S. Cl. ...................... 382/128; 382/189; 348/14.07
(58) Field of Search ................................ 382/128, 129, 382/130, 131, 132, 133, 162, 165, 170, 175, 181, 184, 189, 197, 214, 232, 100; 725/78, 119; 348/14.02, 14.07; 250/582, 458.1, 453.11; 375/220, 136; 340/870.16; 600/490, 300; 345/418, 419, 424, 444, 442, 420, 426, 581, 589, 773

(56) References Cited

U.S. PATENT DOCUMENTS

| | | | | |
|---|---|---|---|---|
| 3,668,307 A | * | 6/1972 | Face et al. ................... | 725/119 |
| 4,051,522 A | * | 9/1977 | Healy et al. .................. | 725/78 |
| 4,564,861 A | * | 1/1986 | Hishinuma et al. .......... | 250/582 |
| 5,007,429 A | * | 4/1991 | Treatch et al. ............... | 600/490 |
| 5,434,611 A | * | 7/1995 | Tamura ....................... | 725/116 |
| 5,469,353 A | * | 11/1995 | Pinsky et al. ................ | 382/131 |
| 5,673,331 A | * | 9/1997 | Lewis et al. ................. | 382/100 |
| 6,171,237 B1 | * | 1/2001 | Avitall et al. ................ | 600/300 |
| 6,190,313 B1 | * | 2/2001 | Hinkle ......................... | 600/300 |
| 6,525,670 B1 | * | 2/2003 | Doi et al. .............. | 340/870.16 |

FOREIGN PATENT DOCUMENTS

| | | |
|---|---|---|
| JP | 05-049603 | 3/1993 |
| JP | 07-019814 | 1/1995 |
| JP | 07-236614 | 9/1995 |
| JP | 08-215151 | 8/1996 |
| JP | 10-293813 | 11/1998 |
| JP | 11-150699 | 6/1999 |

OTHER PUBLICATIONS

Japanese Office Action for JP 2000–266692 dated May 18, 2004.

* cited by examiner

Primary Examiner—Yon J. Couso
Assistant Examiner—Seyed Azarian
(74) Attorney, Agent, or Firm—RatnerPrestia

(57) ABSTRACT

A data input apparatus that includes an image acquiring unit for acquiring the image of data displayed on the data display section of a measuring instrument, a number reading unit for reading numbers in the above described acquired image and a display unit for displaying the numbers read, with the above described image acquiring unit also acquiring the image of a portion other than the data display section of the above described measuring instrument at the same time, the image recognition unit reading information on the above described measuring instrument other than the above described numbers from the acquired image and the information on the read measuring instrument being used when the above described number reading unit reads numbers.

8 Claims, 33 Drawing Sheets

Fig. 7
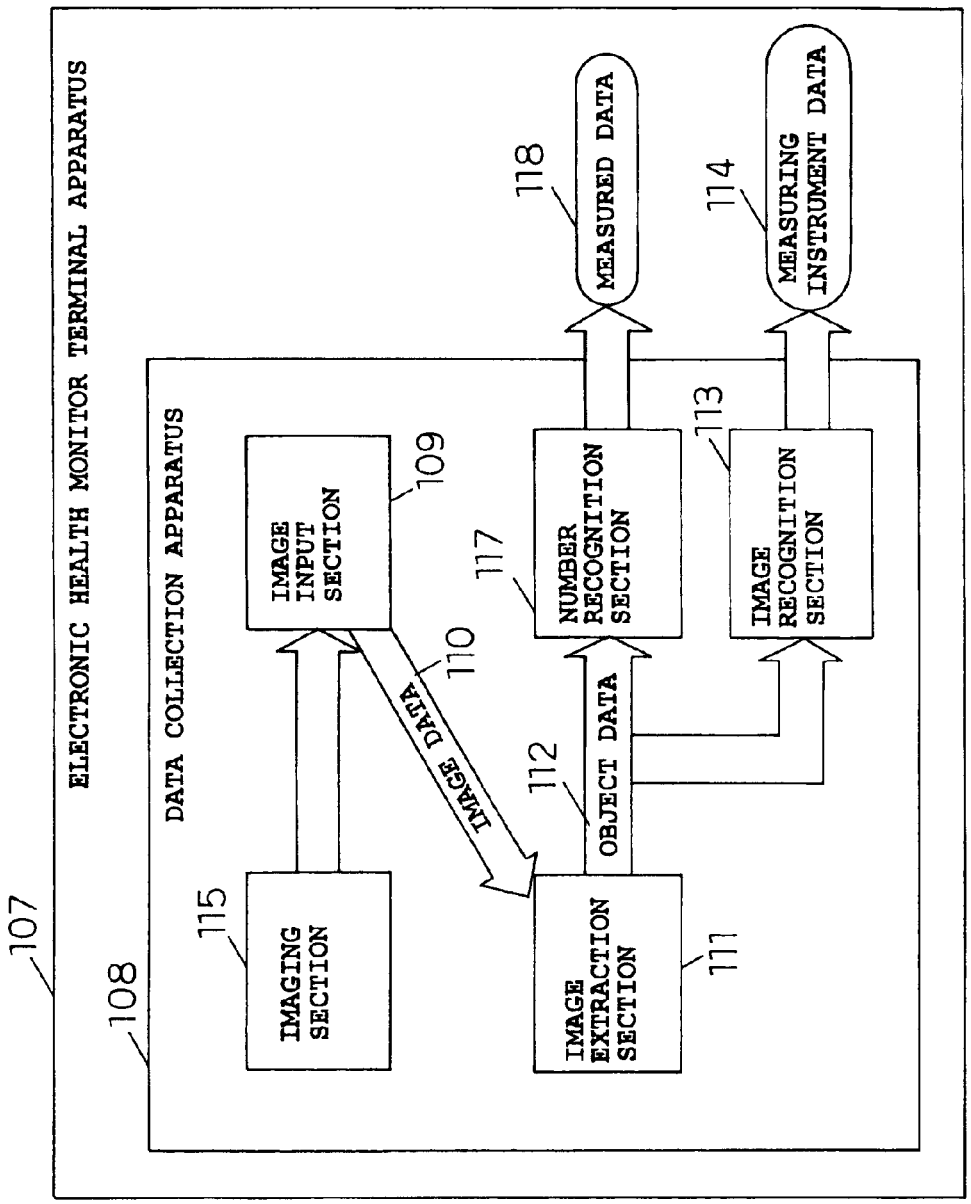
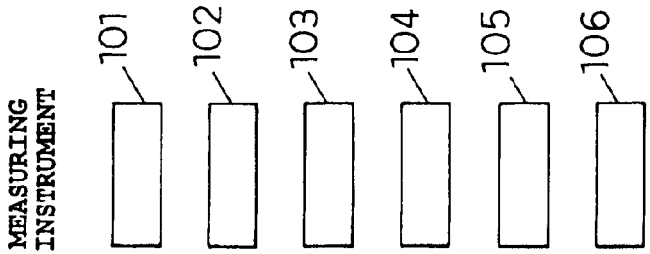

Fig. 30
EXAMPLE 1
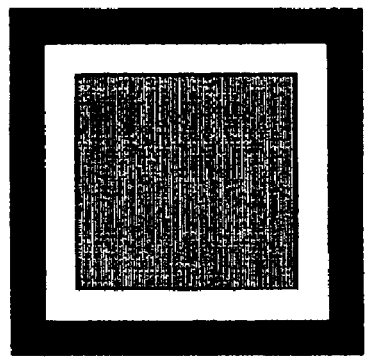
EXAMPLE 2
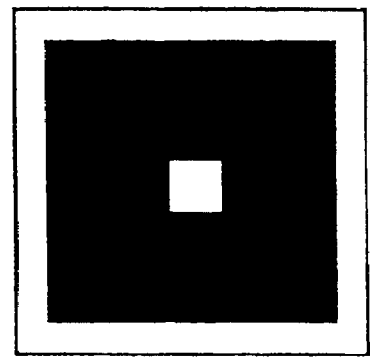
EXAMPLE 3
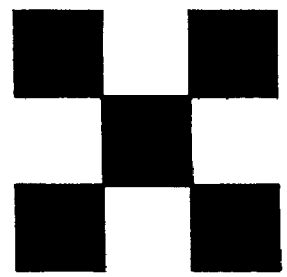
EXAMPLE 4
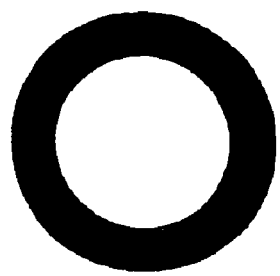

DATA INPUT APPARATUS, DATA INPUT SYSTEM, DISPLAYED DATA ANALYZING APPARATUS AND MEDIUM

BACKGROUND OF THE INVENTION

1. Field of the Invention

The present invention relates to a data input apparatus and a display data analysis apparatus that analyzes measured data used for an electronic health monitor terminal apparatus or the like with various measuring instruments carrying out health check.

2. Related Art of the Invention

FIG. 17 is a block diagram of a conventional electronic health monitor terminal apparatus. An electronic health monitor terminal apparatus is a terminal apparatus to collect various data about a user's health. Checking the user's health requires various data and the electronic health monitor terminal apparatus is equipped with a variety of measuring instruments and their output system also has a great variety. For this reason, the terminal main unit is provided with an interface to allow various data inputs.

FIG. 17 shows a sphygmomanometer 201, a clinical thermometer 202, a uroscopic meter 203, a pedometer 204, scales 205, an adipometer 206 and an electrocardiograph 207, and a data collection apparatus 209 in a terminal main unit 208 is equipped with an infrared receptor 210, a serial I/F 211, a keyboard 212 and optical communication I/F 213 to collect such output data.

The sphygmomanometer 201 is linked with the terminal main unit 208 by means of infrared radiation. The clinical thermometer 202 is connected to the terminal main unit 208 via a serial cable. The electrocardiograph 207 is connected to the terminal main unit 208 via an optical cable.

The user measures his/her health condition using these measuring instruments.

After measuring a blood pressure, data is input through an infrared communication. After measuring a body temperature, data is input through a serial communication. After measuring urine sugar, the number of steps, weight and fat, the user himself/herself reads the data from a data display section and enters the data from the keyboard 212. Since the electrocardiograph is connected to the computer system main unit via an optical communication cable, the measured data is sent to the computer system at all times.

In this way, the terminal main unit receives data inputs through an infrared communication, serial communication, optical communication and manual entries.

However, the conventional electronic health monitor has the following problems:

Firstly, both a measuring instrument and computer system must have hardware for communications, which causes high cost.

When an infrared, optical or serial communication is performed between a measuring instrument and computer system, each communication requires communication hardware at both ends. In the case of measuring instruments in particular, general measuring instruments are usually not provided with such a communication apparatus and it is easily imaginable that an addition of such communication hardware will result in extremely high cost.

Secondly, entering data from the keyboard itself is liable to erroneous inputs.

Handling the keyboard also requires experience on the user part and is also subject to personal preferences, and therefore it is not an input apparatus acceptable by everybody. Especially visually impaired people can not use it. Moreover, when the user reads measured data by his/her eyes and inputs the data from the keyboard, input errors are inherent in human intervention.

Thirdly, connection between a measuring instrument and the terminal main unit via a cable involves complicated routing. Cable connections are obtrusive whether the instrument is used or not, and their length itself is limited and the user must be within a certain distance from the terminal, which is disadvantageous in respect of configurations.

SUMMARY OF THE INVENTION

The present invention has been implemented taking into account the conventional problems described above and it is an object of the present invention to provide an electronic health monitor terminal apparatus capable of implementing measuring instruments and a computer system with a reduced amount of hardware, low costs and simplified data inputs aimed is:

The present invention is a data input apparatus comprising:

image acquiring means for acquiring an image of data displayed on a data display section of a measuring instrument;

number reading means for reading numbers in said acquired image; and displaying means for displaying the read numbers.

The configuration of the present invention eliminates the need to make a connection and communication between the measuring instruments and terminal main unit whether wired or wireless, that is, the need to provide hardware for communications between the measuring instruments and terminal main unit.

Moreover, the present invention eliminates the need for the work to provide software commonality for communications between measuring instruments, making it possible to drastically reduce software development cost.

Furthermore, the present invention allows data to be input by extracting from image data, providing an extremely simple way of input, available to all kinds of people.

The present invention is a display data analysis apparatus that analyzes measured data measured and displayed by a predetermined measuring apparatus and outputs the analysis result to a predetermined processing apparatus, comprising:

imaging means for picking up an image;

detecting means for detecting the measured data displayed by said measuring apparatus in the image picked up by said imaging means using detection auxiliary information to detect the measured data displayed by said measuring apparatus;

analyzing means for analyzing the measured data in the image picked up by said imaging means using analysis auxiliary information to analyze the measured data displayed by said measuring apparatus in the case where said measured data is detected by said detecting means; and outputting means for outputting the analysis result analyzed by said analyzing means.

The display data analysis apparatus of the present invention allows data to be delivered from the measuring instruments side to the host side without the need to prepare a special interface such as RS-232C on the measuring instrument side.

BRIEF DESCRIPTION OF THE DRAWINGS

FIG. 7 is a block diagram showing an electronic health monitor terminal apparatus according to Embodiment 9 of the present invention;

FIG. 30 illustrates some examples of color markers;

Figure 1:
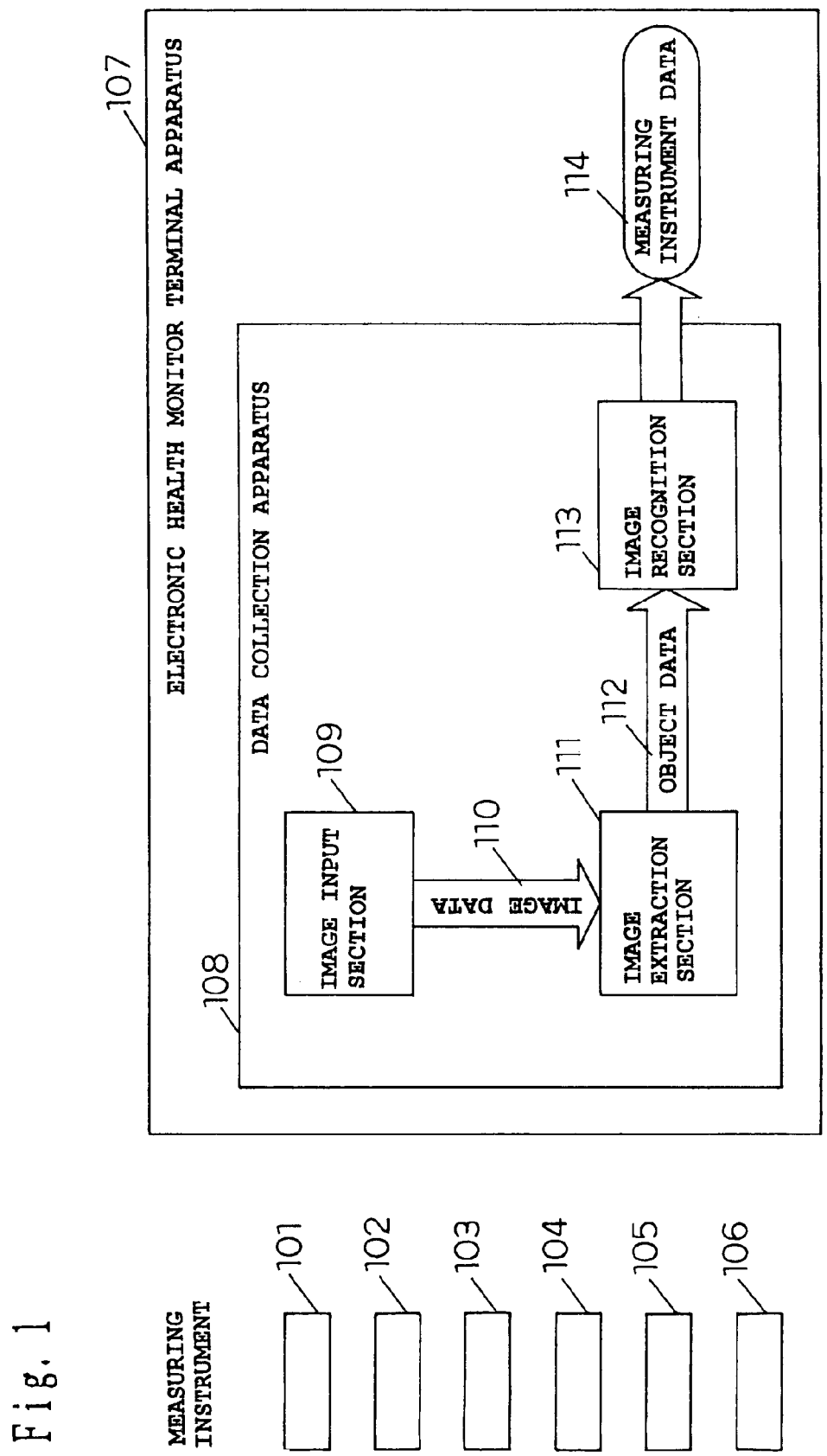
FIG. 1 is a block diagram showing an electronic health monitor terminal apparatus according to Embodiment 1 of the present invention.

| Reference numerals | |
|---|---|
| 101 to 106 | Measuring instruments |
| 107 | Electronic health monitor terminal apparatus |
| 108 | Data collection apparatus |
| 109 | Image input section |
| 110 | Image data |
| 111 | Image extraction section |
| 112 | Object data |
| 113 | Image recognition section |
| 114 | Measuring instrument data |
| 115 | Imaging section |
| 116 | Database section |
| 117 | Number recognition section |
| 118 | Measured data |
| 119 | Analog data reading section |
| 120 | Imaging apparatus |
| 121 | Switch |
| 122 | Data collection apparatus |
| 123 | TV telephone apparatus |
| 124 | Affected area pickup apparatus |
| 1 | Measuring instrument |
| 13 | Measured data display screen |
| 20 | Marker |
| 21 | Corner marker |
| 22 | L marker |
| 23 | Color marker |
| 24 | Code marker |
| 301 | Image input section |
| 304 | Image analysis apparatus |
| 306 | Analysis result output section |
| 401 | Marker recognition section |
| 402 | Symbol marker information recognition section |
| 403 | Image recognition section |
| 404 | Attribute storage section |
| 1001 | Display data analysis apparatus |

PREFERRED EMBODIMENTS OF THE INVENTION

With reference now to FIG. 1 to FIG. 16, embodiments of the present invention will be explained below.

(Embodiment 1)

FIG. 1 is a block diagram corresponding to an electronic health monitor terminal apparatus as an embodiment of data input apparatus according to the present invention.

The terminal apparatus includes measuring instruments 101 to 106 and a data collection apparatus 108. The measuring instruments 101 to 106 are a sphygmomanometer 101, a clinical thermometer 102, a uroscopic meter 103, a pedometer 104, and scales 105, which are used to measure the user's health condition.

In addition to those described above, the measuring instruments 101 to 106 can also be any instruments such as an adipometer and a blood sugar meter.

The data collection apparatus 108 includes an image input section 109 that captures image data, an image extraction section 111 that extracts an object from the captured image and outputs object data 112 and an image recognition section 113 that identifies the measuring instrument in the image data from the object data 112 and outputs measuring instrument data 114 specific to the measuring instrument.

The image input section 109 is an apparatus like a scanner capable of generating image data 110.

The image recognition section 113 can perform shape recognition that recognizes a measuring instrument from the color and shape in the object data 112.

The method of inputting measuring instrument data in the electronic health monitor terminal apparatus with the above configuration will be explained below.

The user selects one measuring instrument to be used. The user inputs the selected measuring instrument using the image input section 109 as image data. From the captured image data, the image extraction section 111 extracts the object data of the measuring instrument and outputs the object data to the image recognition section 112. Objects in this embodiment refer to the color and shape of a measuring instrument.

The image recognition section 111 recognizes what the measuring instrument whose image has been captured is from the input object data and outputs the measuring instrument data 114.

The measuring instrument data 114 includes a manufacturer's name, type and name of the measuring instrument, measurable items, units of measured data, etc.

When image data is created by the image input section 109, it is not necessary to create image data from the measuring instrument itself, but a still picture of the measuring instrument can also be used.

The electronic health monitor terminal apparatus of this embodiment captures the measuring instrument as image data by the image input section 109, recognizes the measuring instrument in the image from the image data and inputs the measuring instrument data to the terminal main unit.

Therefore, this requires no interface apparatus for communications between the measuring instruments 101 to 106 and the terminal main unit 107, making it possible to reduce the amount of hardware and implement an electronic health monitor terminal apparatus at low cost.

Likewise, no communication I/F is required on the measuring instrument side, either, and for this reason, measuring instruments sold as general-purpose products can be applied as the measuring instruments of this monitor terminal apparatus.

Therefore, even if the measuring instruments are damaged or lost, these can be immediately substituted by products available on the market, reducing maintenance costs in both time and cost.

Furthermore, since the user can input the measuring instrument data by simply letting the image input section capture the measuring instruments as image data, thus implementing an extremely precise/simple system available to all kinds of people of all generations.

(Embodiment 2)

Figure 2:
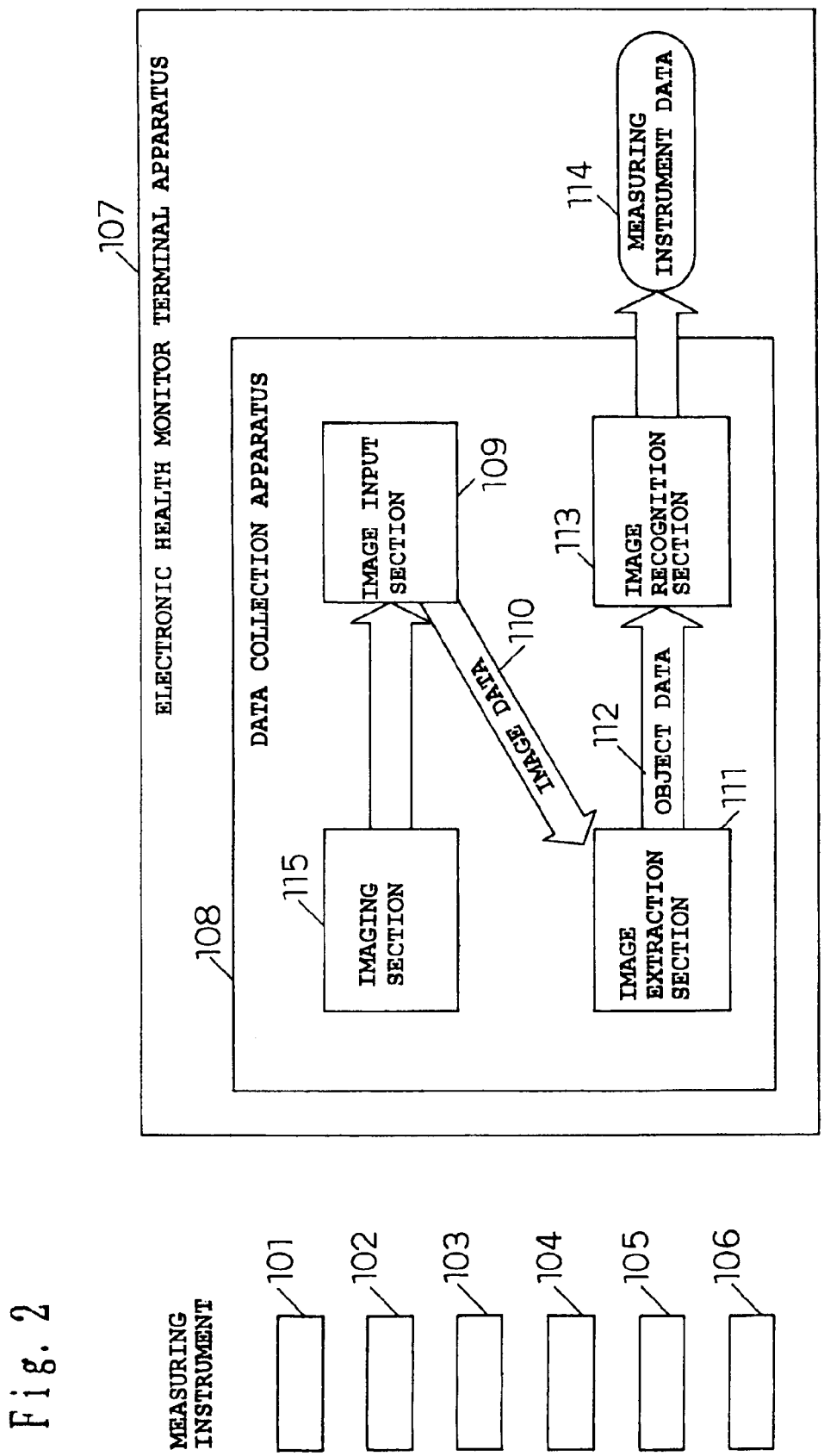
FIG. 2 is a block diagram showing an electronic health monitor terminal apparatus according to Embodiment 2 of the present invention.

FIG. 2 is a block diagram of an electronic health monitor terminal apparatus according to Embodiment 2 of the present invention. This block diagram has an imaging apparatus 115 in addition to the block diagram shown in Embodiment 1.

The imaging apparatus 115 is an apparatus like a CCD camera that can output image data consecutively and the image input section 109 is an apparatus like a capture card to capture the image data as a still picture. The operations and functions of other sections are the similar as those in Embodiment 1.

The method of inputting measuring instrument data in the electronic health monitor terminal apparatus with the above configuration will be explained below.

The user selects one measuring instrument to be used. The user captures the image of the selected measuring instrument the imaging section 115 and lets the image input section 109 capture it as image data 110. From the captured image data 110, the image extraction section 111 extracts object data 112 and outputs it to the image recognition section 113. Objects in this embodiment refer to the color and shape of the measuring instrument.

The image recognition section 113 recognizes what the measuring instrument is from the color and shape of the input object data and outputs the measuring instrument data 114. The measuring instrument data includes a manufacturer's name, type and name of the measuring instrument, measurable items, units of measured data, etc.

In the electronic health monitor terminal apparatus of this embodiment, the imaging section 115 takes a picture of the measuring instrument and the image input section 109 captures it as image data and the measuring instrument in the image is recognized from the image data and the measuring instrument data is input to the terminal main unit.

Therefore, this requires no interface apparatus for communications between the measuring instruments 101 to 106 and the terminal main unit 107, making it possible to reduce the amount of hardware and implement an electronic health monitor terminal apparatus at low cost.

Likewise, no communication I/F is required on the measuring instrument side, either, and for this reason, measuring instruments sold as general-purpose products can be applied as the measuring instruments of this monitor terminal apparatus.

Therefore, even if the measuring instruments are damaged or lost, these can be immediately substituted by products available on the market, reducing maintenance costs in both time and cost.

Furthermore, since the user can input the measuring instrument data by simply letting the image input section capture the measuring instruments as image data, thus implementing an extremely precise/simple system available to all kinds of people of all generations.

Moreover, the input section 109 can capture the image of the measuring instrument from the imaging section 115 while the user's visually checking the image of the measuring instrument, and therefore can capture image data more reliably.

(Embodiment 3)

Figure 3:
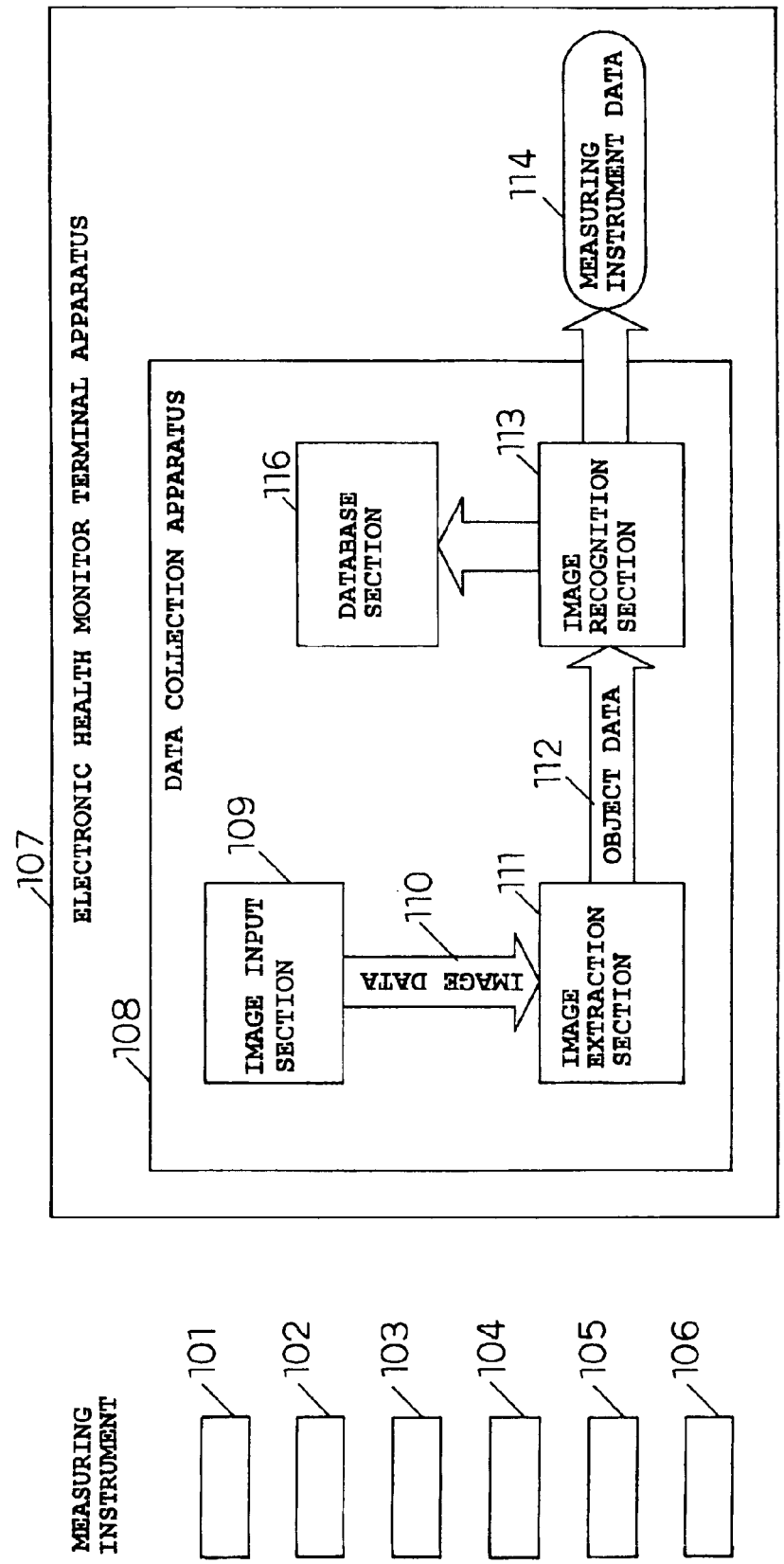
FIG. 3 is a block diagram showing an electronic health monitor terminal apparatus according to Embodiment 3 of the present invention.

FIG. 3 has a database section 116 added to the image recognition section 113 in addition to Embodiment 1.

The database section 116 can store shape data of measuring instruments and add shape data about additional measuring instruments. The image recognition section 113 can recognize more diverse measuring instruments by searching the database section 116. The operations of the sections are the same as those in Embodiment 1 except the database section 114. These operations will be described below.

The user selects one measuring instrument to be used. The input section 109 converts the selected measuring instrument to image data 110. The image data is input to the image extraction section 111 and the image extraction section 111 extracts the object data of the measuring instrument from the image data and outputs the object data to the image recognition section 113. Objects in this embodiment refer to the color and shape of a measuring instrument.

The image recognition section 111 recognizes what the measuring instrument is by searching the input object data from the database section 114 and outputs the measuring instrument data. The measuring instrument data includes a manufacturer's name, name of the measuring instrument, measurable items, units of measured data, etc.

When a new measuring instrument is introduced, it is immediately available to the electronic health monitor terminal apparatus of this embodiment by registering the image data in the database section 111. In the case where the measuring instrument in use is broken and a newly purchased different measuring instrument is used, the new measuring instrument is made available if its shape data is registered. In this way, maintenance of the database section 111 makes it extremely easy to add or change measuring instruments.

(Embodiment 4)

In Embodiment 4, the object data in Embodiment 1 is a symbol in one-to-one correspondence with a measuring instrument. The symbol is, for example, a barcode. The image extraction section 111 extracts the barcode and the image recognition section 113 reads a barcode and converts it to measuring instrument data 114.

Since the object data are symbols such as barcodes, it is possible to simplify processing in the image extraction section 111 and the image recognition section 113, allowing processing with hardware at lower cost.

(Embodiment 5)

In Embodiment 5, as in the case of Embodiment 4, the object data in Embodiment 2 is a symbol in one-to-one correspondence with a measuring instrument. The symbol is, for example, a barcode. The image extraction section 111 extracts a barcode and the image recognition section 113 reads the barcode and converts it to measuring instrument data 114.

As in the case of Embodiment 4, since the object data are symbols such as barcodes, it is possible to simplify processing in the image extraction section 111 and the image recognition section 113, allowing processing with hardware at lower cost.

(Embodiment 6)

Figure 4:
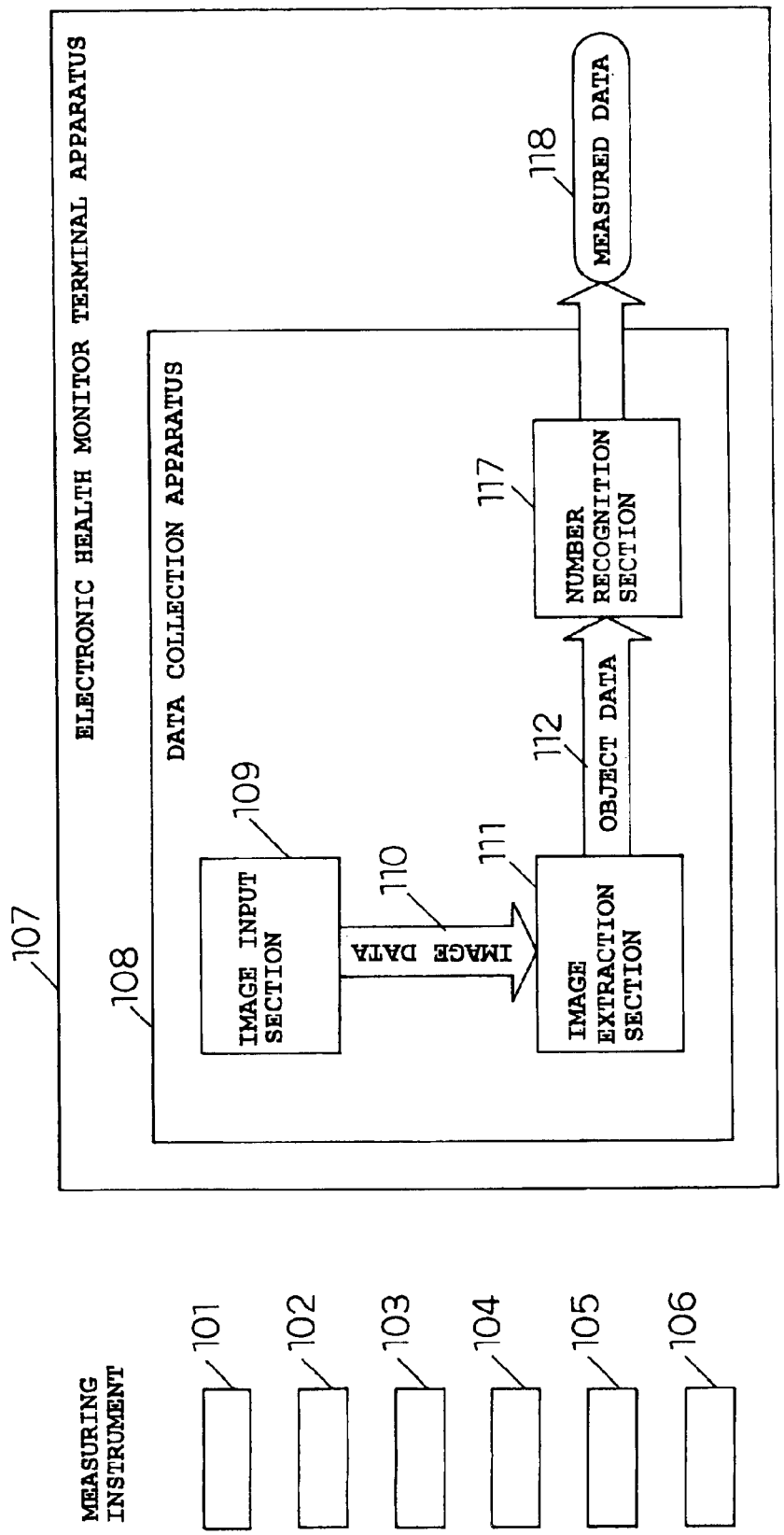
FIG. 4 is a block diagram showing an electronic health monitor terminal apparatus according to Embodiment 6 of the present invention.

FIG. 4 is block diagram showing an electronic health monitor terminal apparatus as an embodiment of the data input apparatus of the present invention. A terminal apparatus 109 includes measuring instruments 101 to 106 and a data collection apparatus 108. The measuring instruments are a sphygmomanometer 101, a clinical thermometer 102, a uroscopic meter 103, a pedometer 104 and scales 105 and these instruments are used to measure the user's health condition. In addition to the measuring instruments mentioned above, there can also be other instruments such as an adipometer and blood sugar meter.

The data collection apparatus 108 includes an image input section 109 that captures image data, an image extraction section 111 that extracts an object from the captured image data and outputs object data 112 and a number recognition section 113 that recognizes what the numbers in the image data are from the object data 112 and outputs measured data 118, which is the measurement result.

The image input section 109 is an apparatus like a scanner capable of generating image data 110.

The image extraction section 111 extracts numbers from the digital data display section in the image data and outputs them as object data. The number recognition section 117 recognizes numbers from the object data 112 and outputs them as measured data.

The method of inputting measured data in the electronic health monitor terminal apparatus with the above configuration will be explained.

The user selects one measuring instrument to be used. The user measures his/her own health condition using the selected measuring instrument. When the measurement is completed, the image input section 109 captures the digital display section as image data. The image extraction section 111 extracts numbers within the digital display section in the image data. Then, the number recognition section 117 recognizes the extracted numbers and outputs them as measured data 118.

In this embodiment, the image input section 109 captures the digital display section as image data, extracts and recognizes numbers from the image data and inputs the measured data to the terminal main unit.

This eliminates the need for an interface apparatus for communications between the measuring instruments 101 to 106 and the terminal main unit 107, making it possible to reduce hardware and implement an electronic health monitor terminal apparatus at low cost.

Likewise, no communication I/F is required on the measuring instrument side, either, and for this reason, measuring instruments sold as general-purpose products can be applied as the measuring instruments of this monitor terminal apparatus.

Therefore, even if the measuring instruments are damaged or lost, these can be immediately substituted by products available on the market, reducing maintenance costs in both time and cost.

Furthermore, since the user can input the measuring result by simply capturing the digital display section of the measuring instrument as image data, thus implementing an extremely precise/simple system available to all kinds of people of all generations.

(Embodiment 7)

Figure 5:
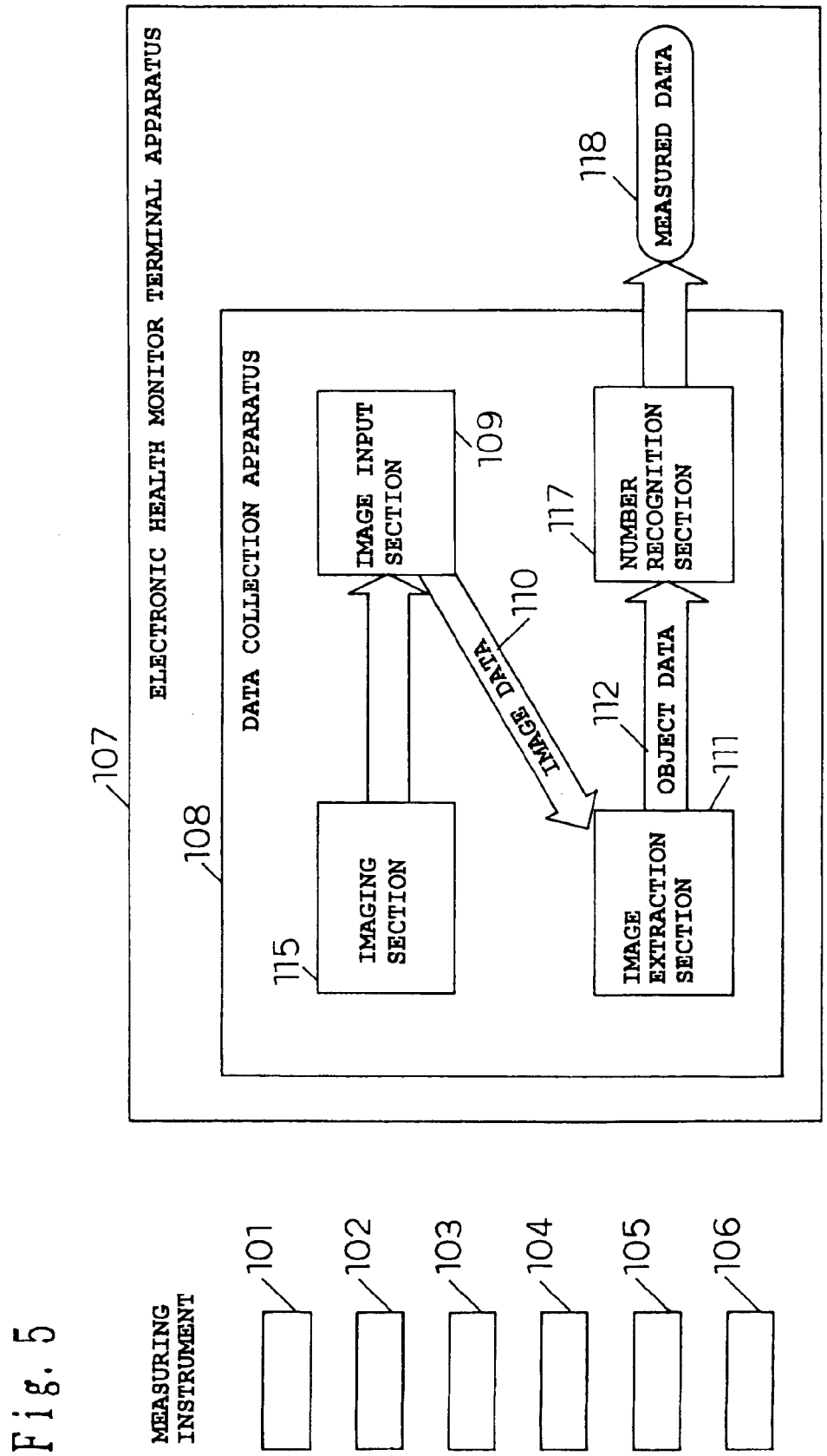
FIG. 5 is a block diagram showing an electronic health monitor terminal apparatus according to Embodiment 7 of the present invention.

FIG. 5 is a block diagram of an electronic health monitor terminal apparatus as an embodiment of the data input apparatus of the present invention.

This block diagram has an imaging apparatus 115 in addition to the block diagram shown in Embodiment 6. The imaging apparatus 115 is an apparatus like a CCD camera that can output image data consecutively and the image input section 109 is an apparatus like a capture card to capture the image data as a still picture. The operations and functions of other sections are the same as those in Embodiment 6.

The method of inputting measured data in the electronic health monitor terminal apparatus with the above described configuration will be explained below.

The user selects one measuring instrument to be used and measures his/her health condition. After completion of measurement, the user takes a picture of the digital display section using the imaging section 115 and captures the image data using the image input section 109. The image data is an image including numbers that display the measurement result of the measuring instrument. The image extraction section 111 extracts numbers and the number recognition section 117 recognizes them and inputs the measured data to the terminal apparatus.

In addition to the features shown in Embodiment 6, the electronic health monitor terminal apparatus of this embodiment captures image data using the imaging section 115, making it possible to capture the image while a user visually checks the image from the terminal main unit and capture image data more securely.

(Embodiment 8)

Figure 6:
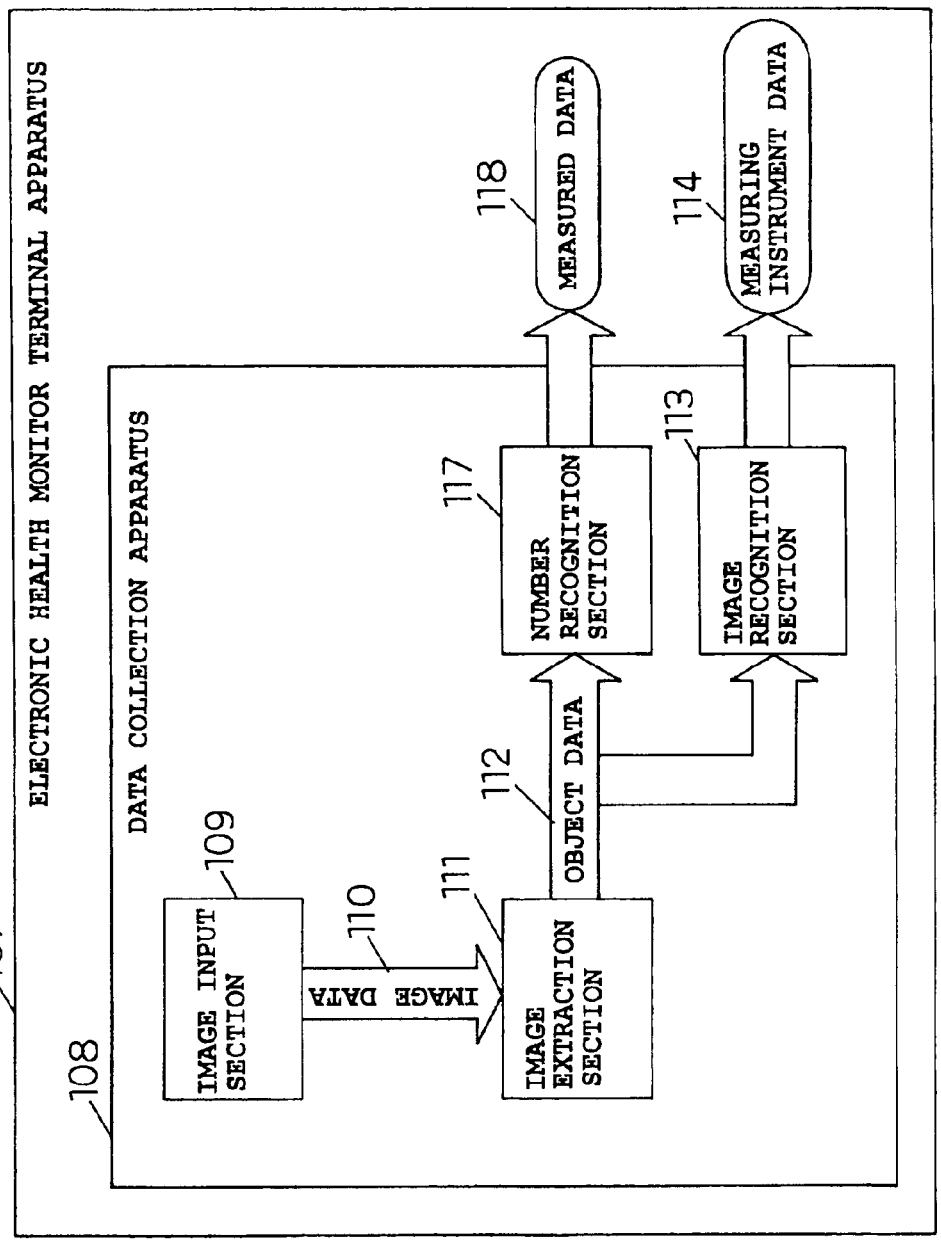
FIG. 6 is a block diagram showing an electronic health monitor terminal apparatus according to Embodiment 8 of the present invention.

FIG. 6 is block diagram showing an electronic health monitor terminal apparatus as en embodiment of the data input apparatus according to the present invention. A terminal apparatus 109 includes measuring instruments 101 to 106 and a data collection apparatus 108. The measuring instruments are a sphygmomanometer 101, a clinical thermometer 102, a uroscopic meter 103, a pedometer 104 and scales 105 and these instruments are used to measure the user's health condition. In addition to the measuring instruments mentioned here, there can also be other instruments such as an adipometer and blood sugar meter.

The data collection apparatus 108 includes an image input section 109 that captures image data, an image extraction section 111 that extracts an object from the captured image data and outputs object data 112 and a number recognition section 113 that recognizes what numbers in the image data are from the object data 112 and outputs measured data 118, which is the measurement result, and an image recognition section that recognizes what the measuring instrument in the image data is from the object data 112 and outputs measuring instrument data 114 specific to the measuring instrument.

The image input section 109 is an apparatus like a scanner capable of generating image data 110. The image extraction section 111 extracts numbers, symbols, color and shape in the image data and outputs them as object data. The number recognition section 117 recognizes numbers from the object data 112 and outputs them as measured data. The image recognition section 113 recognizes a measuring instrument from the object data 112 and outputs the measuring instrument data. The measuring instrument data is data including the name of the manufacturer, name of the measuring instrument, measurable data and unit of measured values.

The method of inputting the measuring instrument data and measured data in the electronic health monitor terminal apparatus with the above configuration will be explained.

The user selects one measuring instrument to be used and measures his/her health condition. When the measurement is completed, the image input section 109 captures the image including the distal display section as image data. The image data is an image centered on the digital display section of the measuring instrument and includes numbers, their unit, various symbols/characters and display section as the measurement result. The image extraction section 111 extracts numbers, symbols, characters and the color and shape of the display section from the image data 110 and outputs them as object data. The object data is input to the number recognition section 117 and the image recognition section 113.

The number recognition section 117 recognizes numbers and outputs measured data 118.

The image recognition section 113 recognizes what the measuring instrument is from information such as characters, symbols, shape and color and outputs measuring instrument data 114. That is, these are data such as the unit of the displayed measured numerical values, the name of the manufacturer of the measuring instrument, shape and color of the measuring instrument or barcode corresponding to the type of the measuring instrument.

In this embodiment, the image input section captures the image including the digital display section as the image data, extracts numbers, characters, symbols, color and shape from the image data, recognizes them and inputs the measured data and measuring instrument data to the terminal main unit. When the numbers are read, it is also possible to use the above already read measuring instrument 114. That is, it is possible to know the manufacturer from the measuring instrument data 114 and fonts of the numbers and read numbers more correctly using the font information.

This eliminates the need for an interface apparatus for communications between the measuring instruments 101 to 106 and the terminal main unit 107, making it possible to reduce hardware and implement an electronic health monitor terminal apparatus at low cost.

Likewise, no communication I/F is required on the measuring instrument side, either, and for this reason, measuring instruments sold as general-purpose products can be applied as the measuring instruments of this monitor terminal apparatus.

Therefore, even if the measuring instruments are damaged or lost, these can be immediately substituted by products available on the market, reducing maintenance costs in both time and cost.

Furthermore, since the user can input the measurement result by simply capturing the digital display section as image data, thus implementing an extremely precise/simple system available to all kinds of people of all generations.

It is possible to provide the number recognition section 117 and/or image recognition section 113 for another apparatus (e.g., host server) connected through a communication channel such as the Internet. Of course, extra parts such as connection cords are required.

(Embodiment 9)

FIG. 7 is a block diagram of an electronic health monitor terminal apparatus according to an embodiment of the data input apparatus of the present invention.

This block diagram has an imaging apparatus 115 in addition to the block diagram shown in Embodiment 8. The imaging apparatus 115 is an apparatus like a CCD camera that can output image data consecutively and the image input section 109 is an apparatus like a capture card to capture the image data as a still picture. The operations and functions of other sections are the same as those in Embodiment 8.

The method of inputting measured data in the electronic health monitor terminal apparatus with the above configuration will be explained below.

The user selects one measuring instrument to be used and measures his/her health condition. After completion of measurement, the user captures the digital display section using the imaging section 115 and captures the image data using the image input section 109. The image data is an image centered on the digital display section of the measuring instrument including numbers, their unit, various symbols/characters and display section.

The image extraction section 111 extracts numbers, symbols, characters, color and shape and inputs them to the number recognition'section 117 and image recognition section 113. The number recognition section 117 recognizes numbers and outputs measured data 118. The image recognition section 113 recognizes what the measuring instrument is from information such as characters, symbols, shape and color and outputs measuring instrument data 114.

In addition to the features shown in Embodiment 6, the electronic health monitor terminal apparatus of this embodiment captures image data using the imaging section 115, making it possible to capture the image while a user visually checks the image from the terminal main unit and capture image data more securely.

(Embodiment 10)

Figure 8:
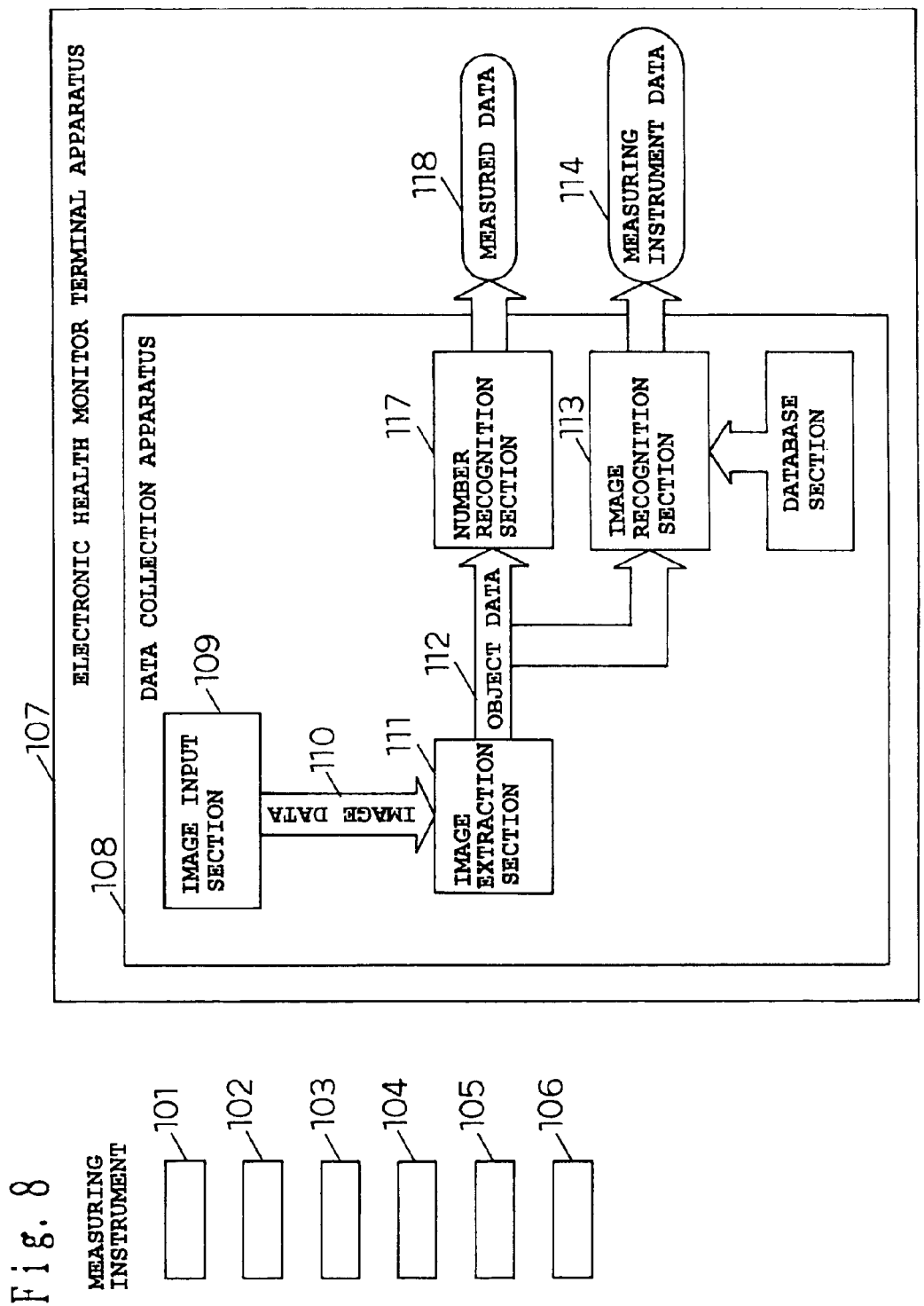
FIG. 8 is a block diagram showing an electronic health monitor terminal apparatus according to Embodiment 10 of the present invention.

FIG. 8 is block diagram of an electronic health monitor terminal apparatus as an embodiment of the data input apparatus of the present invention.

This block diagram has a database section 116 added to the image recognition section 113 in addition to the block diagram shown in Embodiment 8. The database section 116 can store shape data of measuring instruments and add shape data about additional measuring instruments. The image recognition section 113 can recognize more diverse measuring instruments by searching the database section 116. The operations of the sections are the same as those in Embodiment 8 except the database section 114.

These operations will be described below.

The user selects one measuring instrument to be used and measures his/her health condition. When the measurement is completed, the image input section 109 captures the image including the distal display section as image data. The image data is an image centered on the digital display section of the measuring instrument and includes numbers, their unit, various symbols/characters and display section as the measurement results.

The image extraction section 111 extracts numbers, symbols, characters, color and shape of the display section from the image data 110 and outputs them as object data. The object data is input to the number recognition section 117 and the image recognition section 113. The number recognition section 117 recognizes numbers and outputs measurement data 118. The image recognition section 113 searches information such as characters, symbols, shape and color, recognizes what the measuring instrument is and outputs measuring instrument data 114.

When a new measuring instrument is introduced, it is immediately available to the electronic health monitor terminal apparatus of this embodiment by registering the image data in the database section 111. In the case where the measuring instrument in use is broken and a newly purchased different measuring instrument is used, the new measuring instrument is made available by registering the shape data of the new measuring instrument.

In this way, maintenance of the database section 111 makes it extremely easy to add or change measuring instruments.

(Embodiment 11)

In Embodiment 11, the object data in Embodiment 8 is a symbol in one-to-one correspondence with a measuring instrument. The symbol is, for example, a barcode.

The image extraction section 111 extracts a barcode and numbers and the image recognition section 113 converts the barcode to measuring instrument data.

Since the object data are symbols such as barcodes, it is possible to simplify processing in the image extraction section 111 and the image recognition section 113, allowing processing with lower cost hardware.

(Embodiment 12)

In Embodiment 12, the object data in Embodiment 9 is a symbol in one-to-one correspondence with a measuring instrument. The symbol is, for example, a barcode. The image extraction section 111 extracts a barcode and numbers and the image recognition section 113 converts the barcode to measuring instrument data.

Since the object data are symbols such as barcodes, it is possible to simplify processing in the image extraction section 111 and the image recognition section 113, allowing processing with lower cost hardware.

(Embodiment 13)

Figure 9:
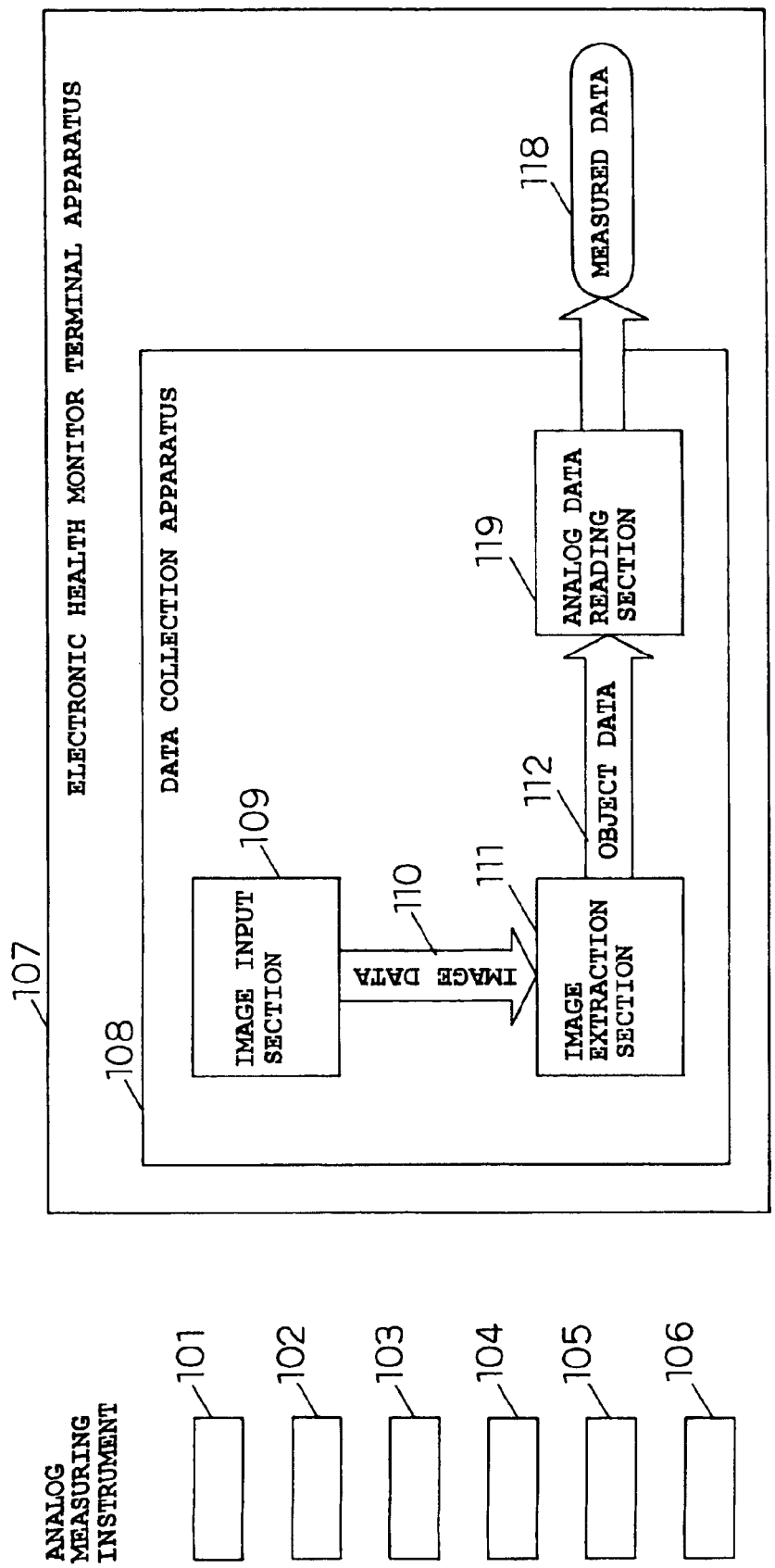
FIG. 9 is a block diagram showing an electronic health monitor terminal apparatus according to Embodiment 13 of the present invention.

FIG. 9 is block diagram showing an electronic health monitor terminal apparatus of an embodiment of the data input apparatus of the present invention.

A terminal apparatus 109 includes measuring instruments 101 to 106 and a data collection apparatus 108. The measuring instruments area sphygmomanometer 101, a clinical thermometer 102, a uroscopic meter 103, a pedometer 104 and scales 105 and these instruments are used to measure the user's health condition and shows the results in analog form.

In addition to the measuring instruments mentioned here, the measuring instruments can also be other instruments such as an adipometer and blood sugar meter.

The data collection apparatus 108 includes an image input section 109 that captures image data, an image extraction section 111 that extracts an object from the captured image data and outputs object data 112 and an analog data reading section 119 that reads the measurement result analog displayed in the image data from the object data 112 and outputs measured data 118. The image input section 109 is an apparatus like a scanner capable of generating image data 110.

The analog data reading section 119 reads data displayed on a scale and outputs the data as measured data.

The method of inputting measured data in the electronic health monitor terminal apparatus with the above configuration will be explained.

The user selects one measuring instrument to be used. The user measures his/her health condition using the selected measuring instrument. When the measurement is completed, the image input section 109 captures the analog display section as image data. The image extraction section 111 extracts the analog display section in the image data. Then, the analog data reading section 119 reads data and outputs it as measured data 118.

In this embodiment, the image input section captures the analog display section as image data, reads the measured value from the image data and inputs the measured data to the terminal main unit.

This eliminates the need for an interface apparatus for communications between the measuring instruments 101 to 106 and the terminal main unit 107, making it possible to reduce hardware and implement an electronic health monitor terminal apparatus at low cost.

Likewise, no communication I/F is required on the measuring instrument side, either, and for this reason, measuring instruments sold as general-purpose products can be applied as the measuring instruments of this monitor terminal apparatus.

Therefore, even if the measuring instruments are damaged or lost, these can be immediately substituted by products available on the market, reducing maintenance costs in both time and cost.

Furthermore, since the user can input the measuring instrument data by simply capturing the analog display section of the measuring instrument as image data, thus implementing an extremely precise/simple system available to all kinds of people of all generations.

(Embodiment 14)

Figure 10:
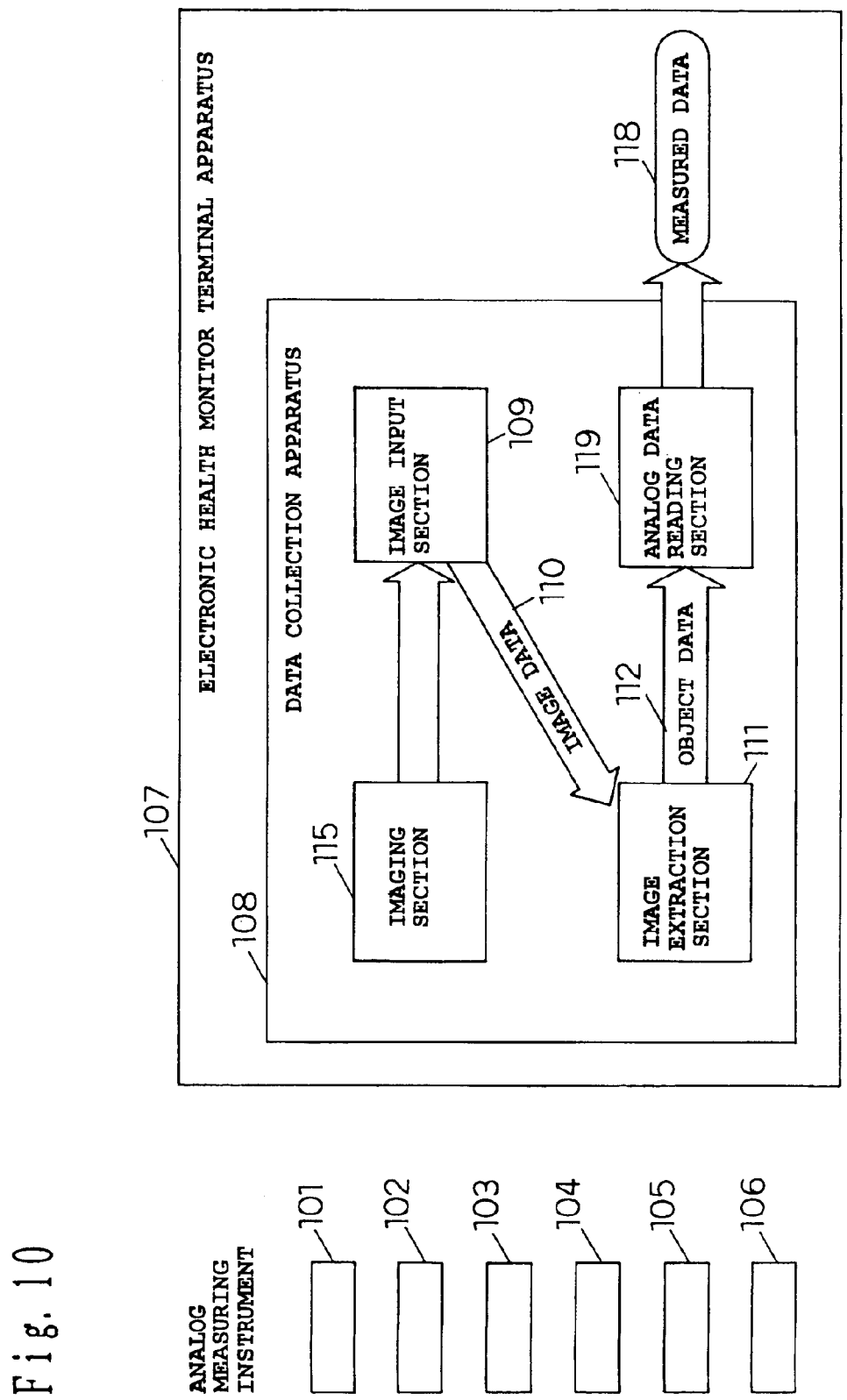
FIG. 10 is a block diagram showing an electronic health monitor terminal apparatus according to Embodiment 14 of the present invention.

FIG. 10 is a block diagram of an electronic health monitor terminal apparatus as an embodiment of the data input apparatus of the present invention.

This block diagram has an imaging apparatus 115 in addition to the block diagram shown in Embodiment 13. The imaging apparatus 115 is an apparatus like a CCD camera that can output image data consecutively and the image input section 109 is an apparatus like a capture card to capture the image data as a still picture. The operations and functions of other sections are the same as those in Embodiment 13.

The method of inputting measured data in the electronic health monitor terminal apparatus with the above configuration will be explained below.

The user selects one measuring instrument to be used and measures his/her health condition. After completion of measurement, the user captures the analog display section using the imaging section 115 and captures the image data using the image input section 109. The image data is an image including the part that displays the measurement result of the measuring instrument in analog form. The image extraction section 111 extracts the analog display section and the analog data reading section 119 reads and inputs the measured data to the terminal apparatus.

In addition to the features shown in Embodiment 13, the electronic health monitor terminal apparatus of this embodiment captures image data using the imaging section 115, making it possible to capture the image while a user visually checks the image from the terminal main unit and capture image data more securely.

(Embodiment 15)

Figure 11:
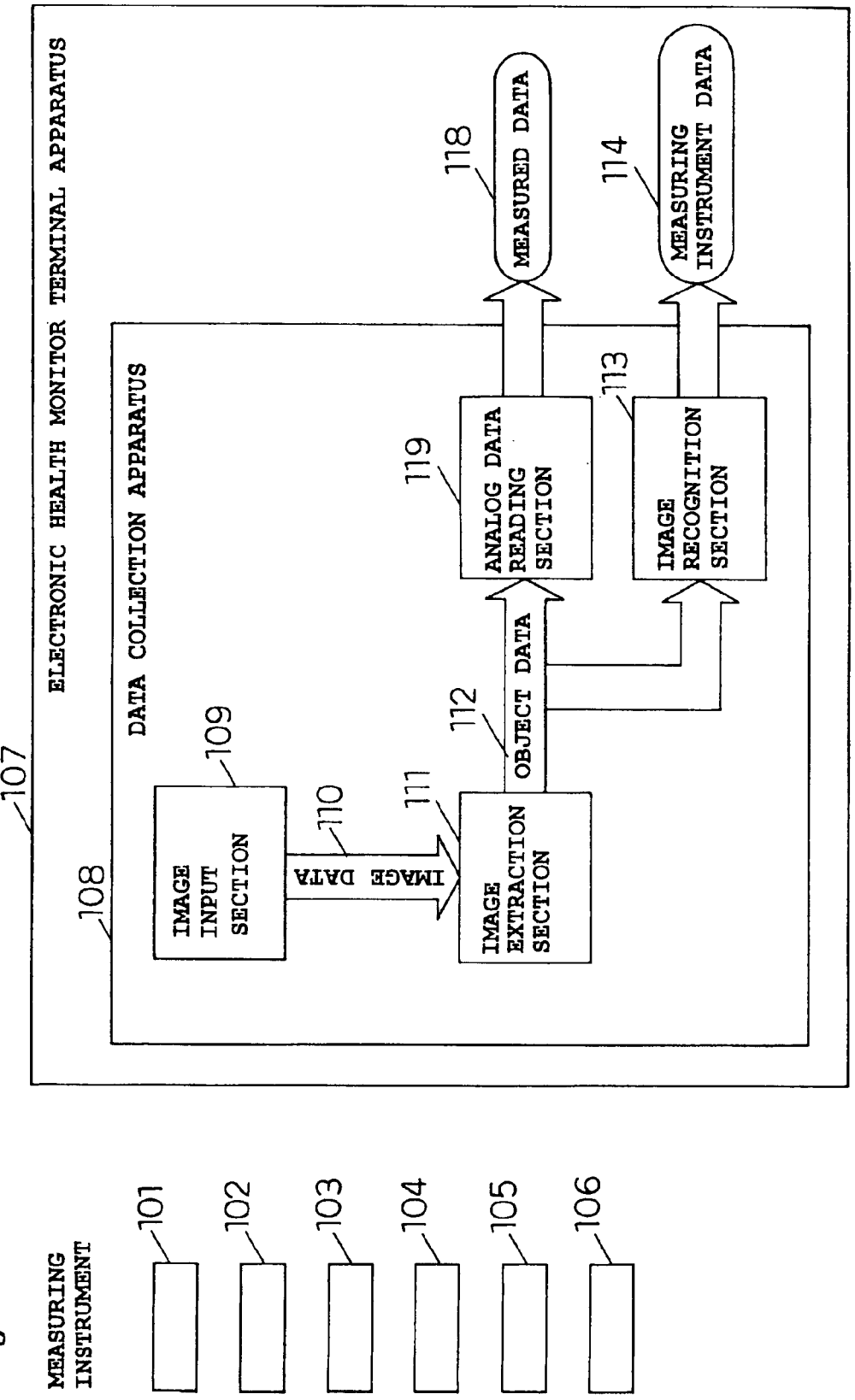
FIG. 11 is a block diagram showing an electronic health monitor terminal apparatus according to Embodiment 15 of the present invention.

FIG. 11 is block diagram showing an embodiment of an electronic health monitor terminal apparatus according to claim 15.

A terminal apparatus 109 includes measuring instruments 101 to 106 and a data collection apparatus 108. The measuring instruments area sphygmomanometer 101, a clinical thermometer 102, a uroscopic meter 103, a pedometer 104 and scales 105 and these instruments are used to measure the user's health condition and display in analog form. In addition to the measuring instruments shown here, there can also be any measuring instruments.

The data collection apparatus 108 includes an image input section 109 that captures image data, an image extraction section 111 that extracts an object from the captured image data and outputs object data 112, an analog data reading section 119 that reads the measurement result of the image data displayed in analog form from the object data 112 and outputs measured data 118 and an image recognition section 113 that recognizes a measuring instrument in the image data from the object data 112 and outputs measuring instrument data 114.

The image input section 109 is an apparatus like a scanner and can create image data 110. The analog data reading section 119 reads data displayed on a scale and outputs as measured data. The image recognition section 113 recognizes the color and shape of the measuring instrument and outputs measuring instrument data.

The method of inputting the measured data in the electronic health monitor terminal apparatus with the above configuration will be explained.

The user selects one measuring instrument to be used and measures his/her own health condition using the selected measuring instrument. When the measurement is completed, the image input section 109 captures the image including the analog display section as image data. The image extraction section 111 extracts the analog display section in the image data, overall shape and color. Then, the analog data reading section 119 reads data and outputs them as measured data 118. At the same time, the extracted object data is also input to the image recognition section 113, where the measuring instrument is recognized from the color and shape and measuring instrument data 113 is output. In this embodiment, the image input section captures the image including the analog display section as image data, reads the measured value from the image data, recognizes the shape and color and the measured data and measuring instrument data are input to the terminal main unit.

This eliminates the need for an interface apparatus for communications between the measuring instruments 101 to 106 and the terminal main unit 107, making it possible to reduce hardware and implement an electronic health monitor terminal apparatus at low cost.

Likewise, no communication I/F is required on the measuring instrument side, either, and for this reason, measuring instruments sold as general-purpose products can be applied as the measuring instruments of this monitor terminal apparatus.

Therefore, even if the measuring instruments are damaged or lost, these can be immediately substituted by products available on the market, reducing maintenance costs in both time and cost. Furthermore, since the user can input the measurement result by simply capturing the analog display section of the measuring instrument as image data, thus implementing an extremely precise/simple system available to all kinds of people of all generations.

(Embodiment 16)

Figure 12:
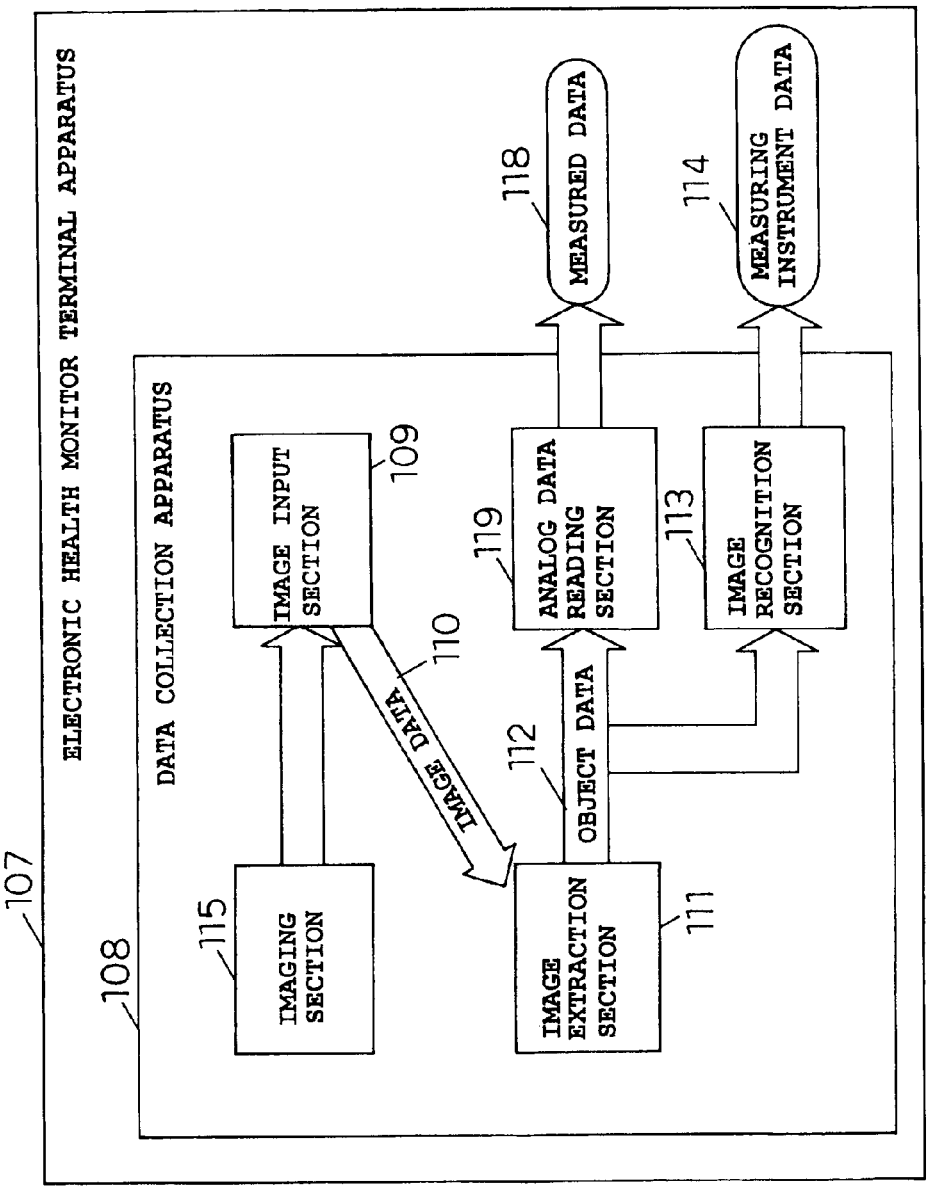
FIG. 12 is a block diagram showing an electronic health monitor terminal apparatus according to Embodiment 16 of the present invention.

FIG. 12 is a block diagram of an electronic health monitor terminal apparatus as an embodiment of the data input apparatus of the present invention. This block diagram has an imaging apparatus 115 in addition to the block diagram shown in Embodiment 15.

The imaging apparatus 115 is an apparatus like a CCD camera that can output image data consecutively and the image input section 109 is an apparatus like a capture card to capture the image data as a still picture. The operations and functions of other sections are the same as those in Embodiment 13.

The method of inputting measured data in the electronic health monitor terminal apparatus with the above described configuration will be explained below.

The user selects one measuring instrument to be used and measures his/her health condition. After completion of measurement, the user captures the part including the analog display section using the imaging section 115 and captures the image data using the image input section 109. The image data is an image including the analog display section of the measurement result of the measuring instrument. The image extraction section 111 extracts the analog display section, color and shape and inputs them to the analog data reading section 119 and image recognition section 113. The analog data reading section 119 reads data from the analog display section and inputs the measured data to the terminal apparatus. The image recognition section 113 recognizes the measuring instrument from the color and shape and outputs the measuring instrument data.

In addition to the features shown in Embodiment 13, the electronic health monitor terminal apparatus of this embodiment captures image data using the imaging section 115, making it possible to capture the image while a user visually checks the image from the terminal main unit and capture image data more securely.

(Embodiment 17)

Figure 13:
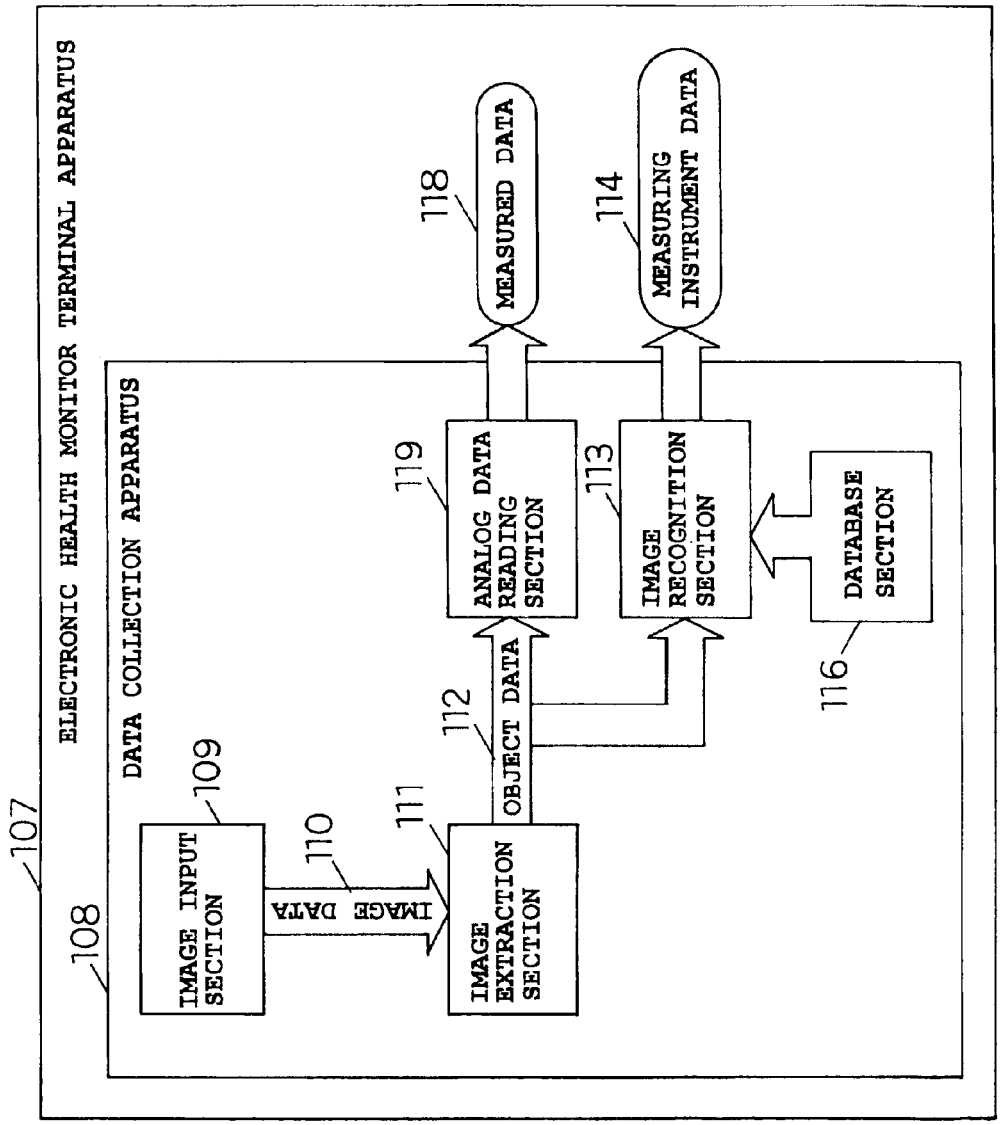
FIG. 13 is a block diagram showing an electronic health monitor terminal apparatus according to Embodiment 17 of the present invention.

FIG. 13 is block diagram of an electronic health monitor terminal apparatus as an embodiment of the present invention. FIG. 13 has a data base section 116 added to the image recognition section 113 in addition to the block diagram shown in Embodiment 15. The database section 116 can store shape data of a measuring instrument and add shape data about additional measuring instruments. The image recognition section 113 can recognize more diverse measuring instruments by searching the database section 116. The operations of the sections are the same as those in Embodiment 15 except the database section 114.

These operations will be described below.

The user selects one measuring instrument to be used and measures his/her health condition. When the measurement is completed, the image input section 109 captures an image including the analog display section as image data. The image data is an image centered on the digital display section of the measuring instrument and includes numbers, their unit, various symbols/characters and display section as the measurement results.

The image extraction section 111 extracts the analog display section, color and shape of the display section from the image data 110 and outputs them as object data. The object data is input to the analog data reading section 119 and the image recognition section 113. The analog-data reading section 119 reads the analog display section and outputs measured data 118. The image recognition section 113 searches information such as the shape and color of the display section from the database section, recognizes what the measuring instrument is and outputs measuring instrument data 114.

When a new measuring instrument is introduced, it is immediately available to the electronic health monitor terminal apparatus of this embodiment by registering the image data in the database section 111. In the case where the measuring instrument in use is broken and a newly purchased different measuring instrument is used, the new measuring instrument is made-available if the shape data of that new measuring instrument is registered.

In this way, maintenance of the database section 11 makes it extremely easy to add or change measuring instruments.
(Embodiment 18)

In Embodiment 18, the object data in Embodiment 15 is not a color or shape, but a symbol in one-to-one correspondence with a measuring instrument and the symbol is, for example, a barcode. The image extraction section 111 extracts a barcode and the analog display section and the image recognition section 113 recognizes the barcode and outputs measuring instrument data 114.

Since the object data are symbols such as barcodes, it is possible to simplify processing in the image extraction section 111 and the image recognition section 113, allowing processing with lower cost hardware.
(Embodiment 19)

In Embodiment 19, the object data in Embodiment 16 is not a color or shape, but a symbol in one-to-one correspondence with a measuring instrument and the symbol is, for example, a barcode.

Since the object data is a symbol such as a barcode, it is possible to simplify processing in the image extraction section 111 and the image recognition section 113, allowing processing with lower cost hardware.
(Embodiment 20)

Figure 14:
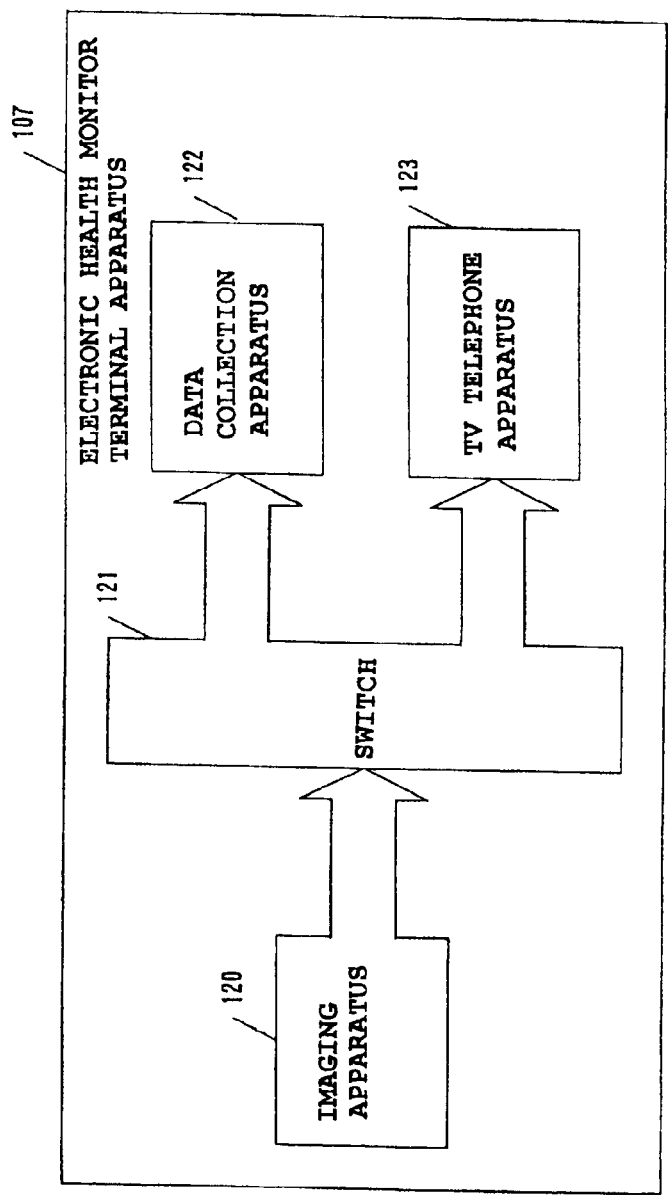
FIG. 14 is a block diagram showing an electronic health monitor terminal apparatus according to Embodiment 20 of the present invention.

FIG. 14 is a block diagram showing an electronic health monitor terminal apparatus as an embodiment of the data input apparatus of the present invention.

A terminal apparatus includes an imaging apparatus 120, a switch 121, a data collection apparatus 122, a TV telephone apparatus 123, and image data output by the imaging apparatus 120 is switched by the switch 121 and input to the data collection apparatus 122 or the TV telephone apparatus 123.

The user switches the output destination of the switch 121 according to the purpose of use. The user measures his/her health condition using measuring instruments and switches the output destination to the data collection apparatus 122 to input data or to the TV telephone apparatus 123 to use the apparatus as a TV telephone to converse with a third party who is in a remote place.

This embodiment allows the imaging apparatus 120 to be shared for different purposes by mode switching, thus implementing a low cost terminal apparatus.
(Embodiment 21)

Figure 15:
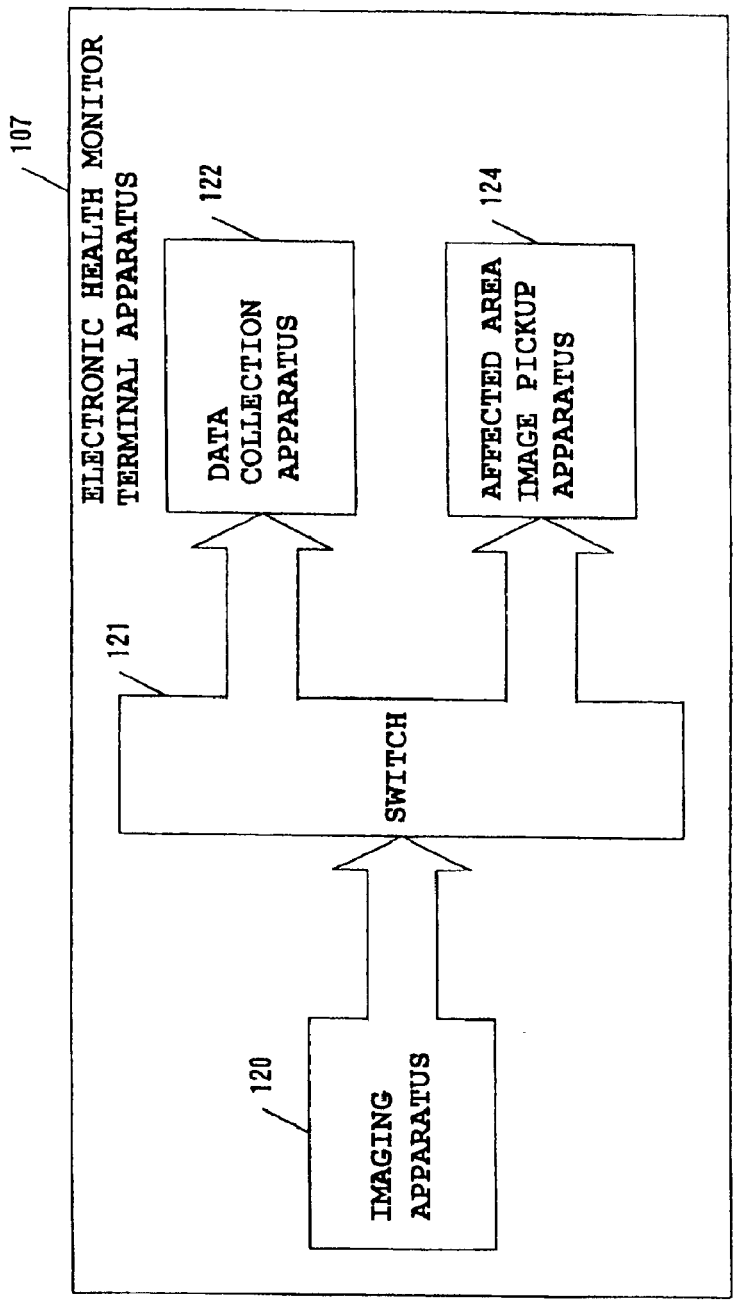
FIG. 15 is a block diagram showing an electronic health monitor terminal apparatus according to Embodiment 21 of the present invention.

FIG. 15 is a block diagram of an electronic health monitor terminal apparatus according to an embodiment of the present invention.

Compared with the block diagram shown in Embodiment 20 in FIG. 14, the TV telephone apparatus 123 is replaced by an affected area pickup apparatus (affected area image data collection apparatus) 124. In this embodiment, the image data captured by the imaging apparatus 120 is switched by the switch 121 and input to the data collection apparatus 122 or the affected area pickup apparatus 124. The affected area pickup apparatus 124 is an apparatus to capture the image of the affected area of the user and a doctor carries out diagnosis using it later.

The user switches the output destination of the switch 121 according to the purpose of use. The user measures his/her health condition using a measuring instrument and switches the output destination to the data collection apparatus 122 to input data and to the affected area pickup apparatus 124 to capture the image of the affected area and wait for a diagnosis by a doctor.

This embodiment allows the imaging apparatus 120 to be shared for different purposes by mode switching, thus implementing a low cost terminal apparatus.
(Embodiment 22)

Figure 16:
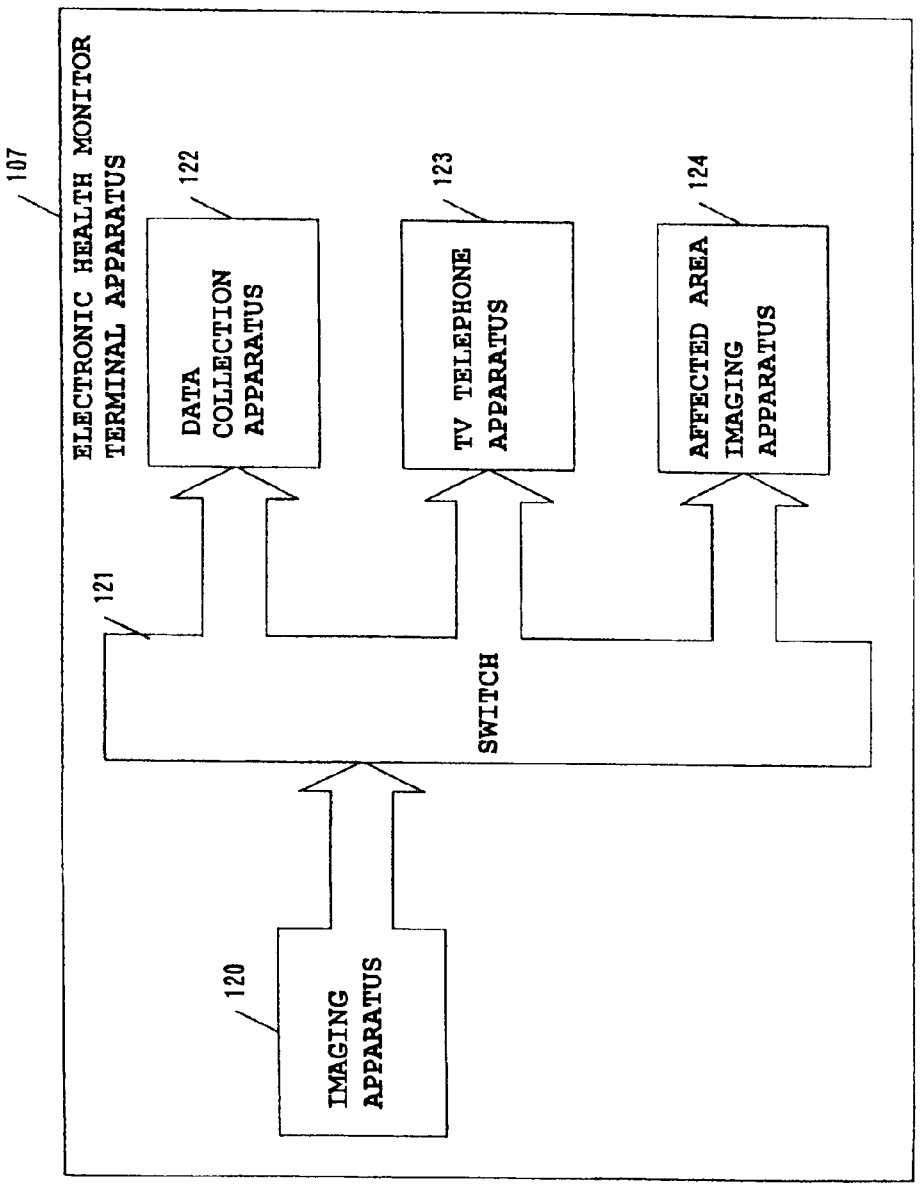
FIG. 16 is a block diagram showing an electronic health monitor terminal apparatus according to Embodiment 22 of the present invention.
Figure 17:
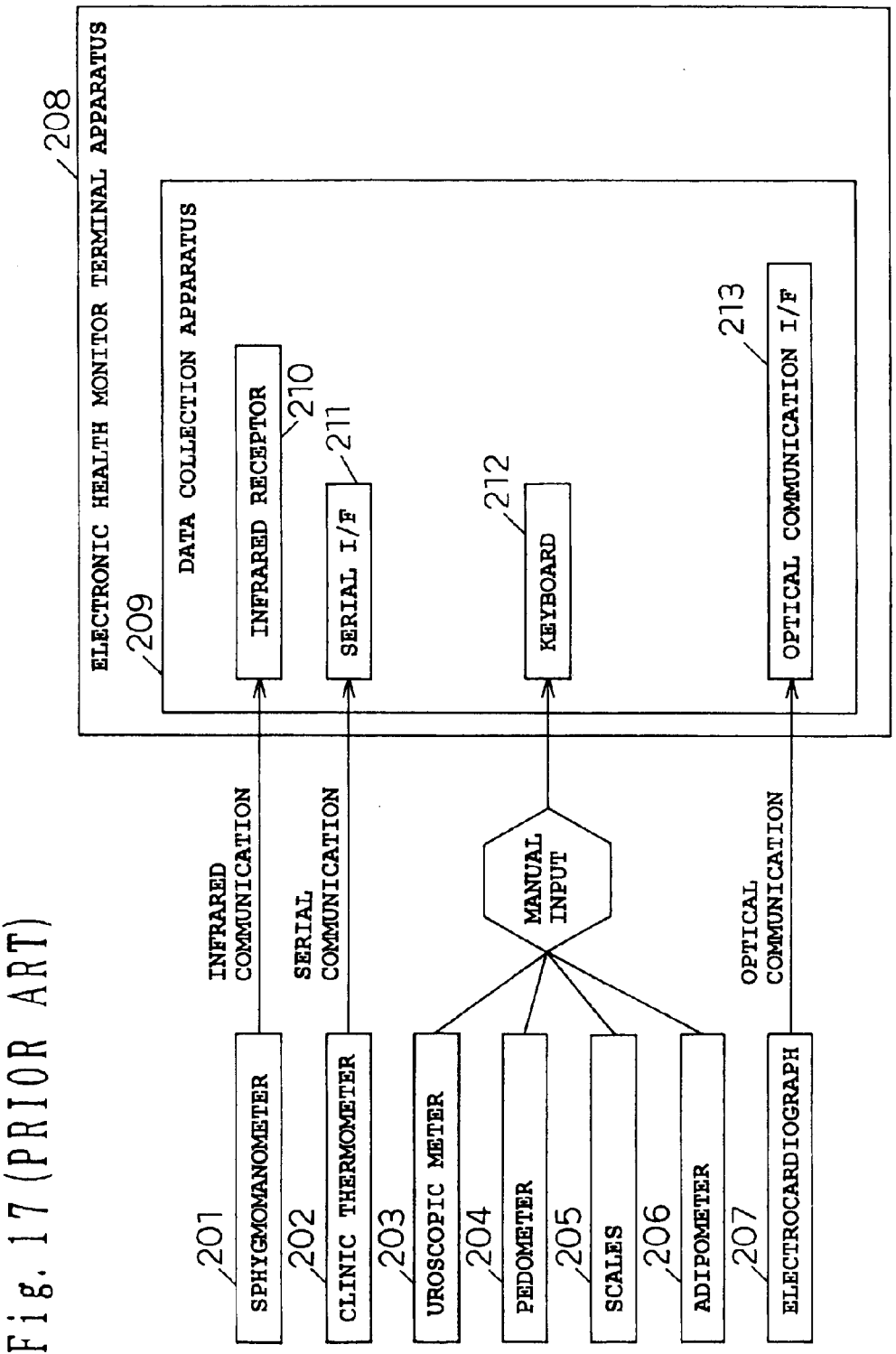
FIG. 17 is a block diagram showing a conventional electronic health monitor terminal apparatus.

FIG. 16 is an embodiment of an electronic health monitor terminal apparatus according to an embodiment of the present invention. Compared with the block diagram shown in Embodiment 20 in FIG. 14, an affected area pickup apparatus 124 is added and the switch 121 can select the output destination of the image data input from one out of the three apparatuses.

The user switches the output destination of the imaging apparatus 120 according to the purpose of use, allowing one apparatus to be shared for different purposes making it possible to implement a low cost terminal apparatus.

Next, another embodiment of the present invention will be explained with reference to the drawings.

Figure 18:
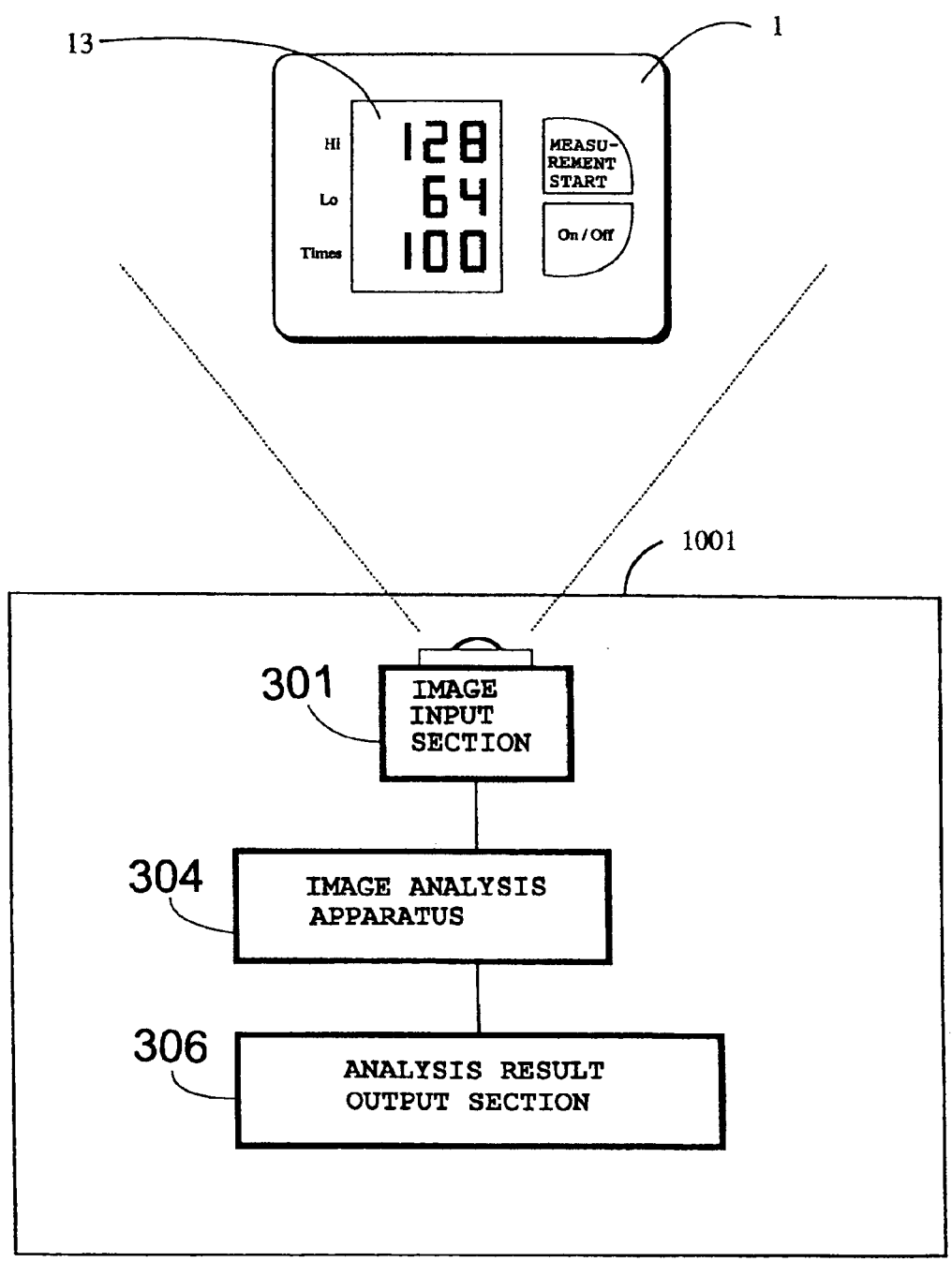
FIG. 18 is a schematic configuration diagram of a display data analysis apparatus of an embodiment of the present invention.

FIG. 18 is a schematic configuration diagram of a display data analysis apparatus of an embodiment of the present invention.

A display data analysis apparatus 1001 of this embodiment is configured by an image input section 301, an image analysis apparatus 304 and an analysis result output section 306. Furthermore, a measuring instrument 1, which is an analysis target, includes a measured data display screen 13 and data that is finally analyzed by the display data analysis apparatus 1001 is the data displayed on the measured data display screen 13 (128, 64 and 100 in FIG. 18).

The image of the measuring instrument 1 acquired by the image input section 301 is analyzed by the image analysis apparatus 304 and its result is output by the analysis result output section 306. Here, as the image input section 301, a means for capturing images such as a CCD camera is used.

Figure 25:
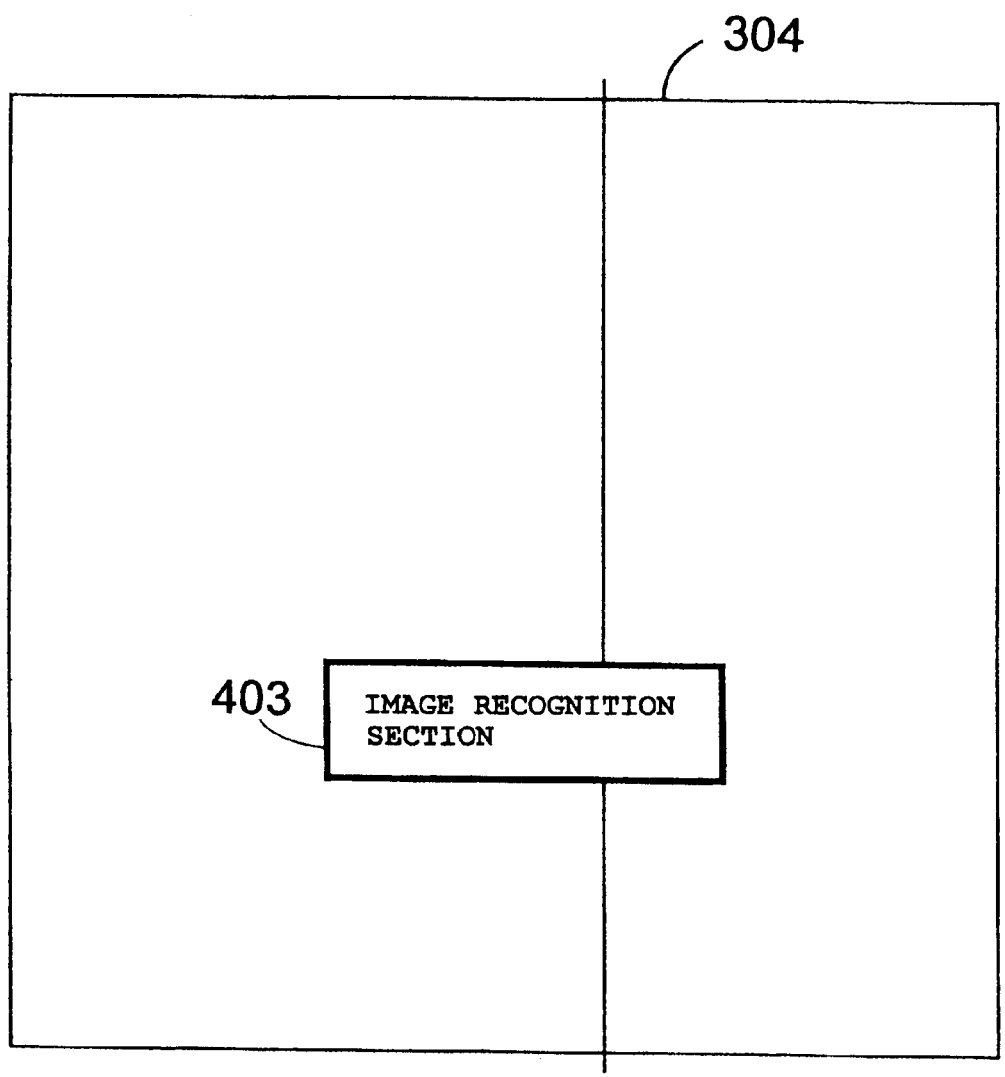
FIG. 25 is a schematic configuration diagram of an image analysis apparatus of the display data analysis apparatus shown in FIG. 18.

The image analysis apparatus 304 incorporates an image recognition section 403 as shown in FIG. 25 and the image analysis apparatus 304 detects and extracts part of the measured data display screen 13 from the captured image and acquires data by extracting/recognizing the data part in the screen 13.

Figure 19:
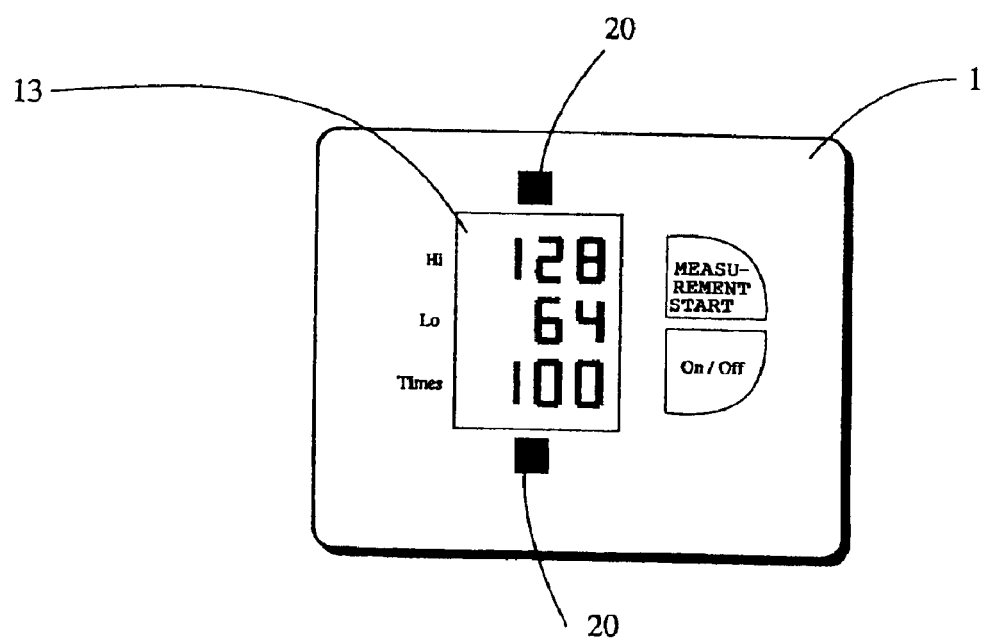
FIG. 19 is a configuration diagram of a measuring instrument with markers attached.
Figure 26:
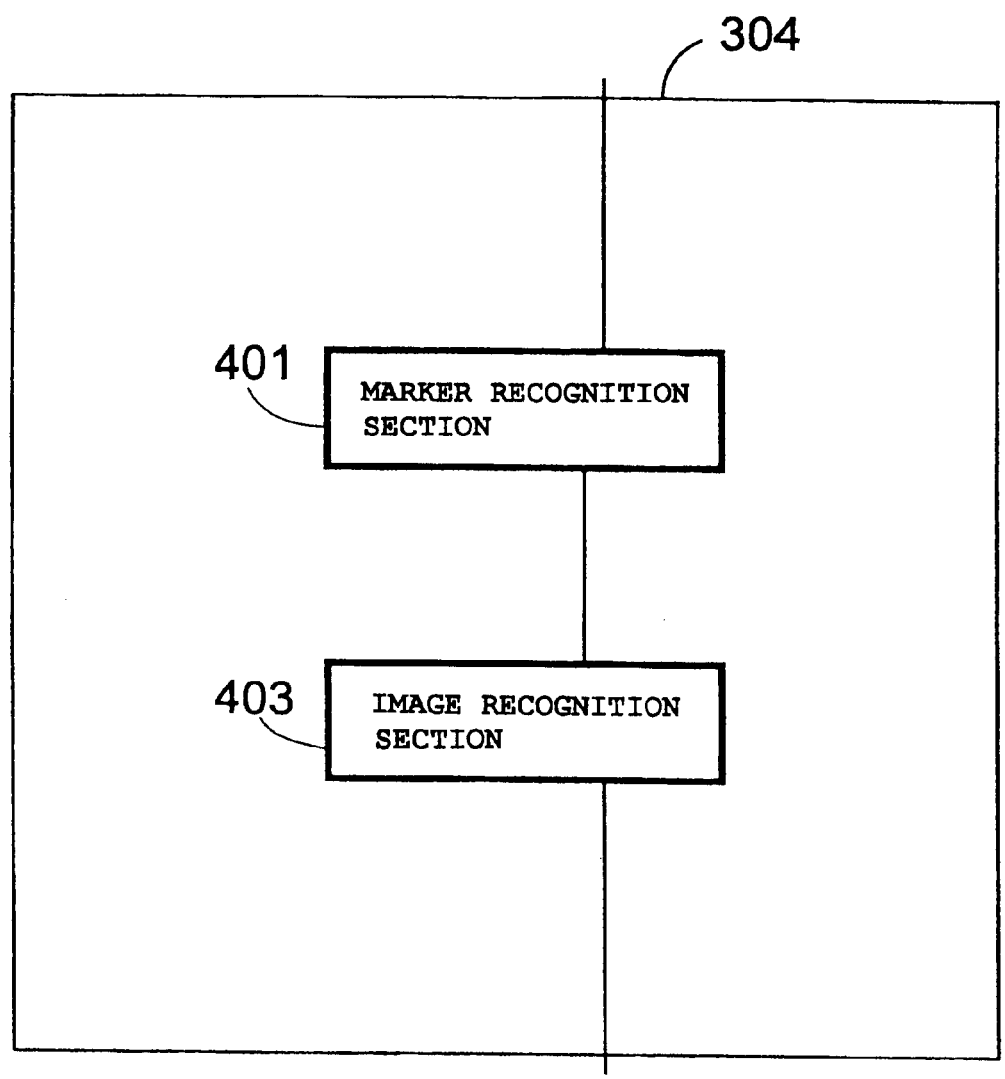
FIG. 26 is a schematic configuration diagram of an image analysis apparatus corresponding to a measuring instrument with at least one of marker, color marker or L marker attached.

Here, FIG. 19 shows a configuration diagram of the measuring instrument 1 that attempts to improve the accuracy of detection of the measured data display screen 13 by the image analysis apparatus 304 by attaching a marker to the measuring instrument 1. In FIG. 19, attaching markers 20 above and below the outside of the measured data display screen 13 of the measuring instrument 1 makes it easier to detect the position of the measured data display screen 13 of the measuring instrument 1 in the image. The configuration of the display data analysis apparatus 1001 in this case is the same as that in FIG. 18. An internal configuration of the image analysis apparatus 304 is as shown in FIG. 26. The image analysis apparatus 304 at this time is configured by a marker recognition section 401 and an image recognition section 403. It is the marker recognition section 401 that actually detects/recognizes the markers 20 in FIG. 19 and the image recognition section 403 performs display/recognition based on the information acquired by the marker recognition section 401.

The marker recognition section 401 detects the measured data display screen 13 using detection auxiliary information to detect the measured data display screen 13 indicating that the part sandwiched by two markers 20 is the measured data display screen 13. This detection auxiliary information is stored, for example, in the marker recognition section 401. The marker 20 is provided with information to identify the type of the measuring instrument 1 to which the markers are attached, for example, a color, and the image recognition section 403 identifies the type of the measuring instrument 1 to which the markers 20 are attached based on differences in colors, etc. of the markers 20 (information to identify the type of the measuring instrument 1).

The image recognition section 403 identifies the type of the measuring instrument 1 to which the markers 20 are attached based on differences in colors, etc. of the markers 20. In the example in FIG. 19, the image recognition section 403 identifies that the measuring instrument 1 to which the markers 20 are attached is a sphygmomanometer based on the color difference of the markers 20. In addition, the image recognition section 403 analyzes numerical values in the measured data display screen 13 using the analysis auxiliary information to identify the meaning of the numerical values in the measured data display screen 13. If an example of the analysis auxiliary information is explained more specifically using FIG. 19, three values 128, 64 and 100 in the measured data display screen 13 constitute the analysis auxiliary information; 128 at the top indicating a higher blood pressure, 64 in the middle indicating a lower blood pressure and 100 at the bottom indicating the heart rate. The image recognition section 403 can also identify the measuring instrument 1 to which the markers 20 are attached based on differences in the attaching position of the markers 20 and differences in the number of markers 20.

Figure 20:
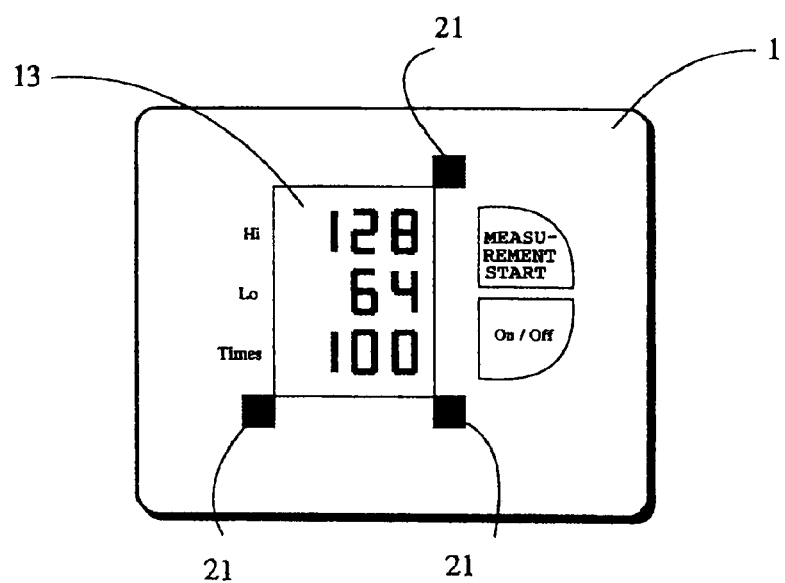
FIG. 20 is a configuration diagram of a measuring instrument with corner markers attached.

FIG. 20 shows that corner markers 21 are attached to the three out of the four corners of the measured data display screen 13, making it easier to detect the measured data display screen 13 in the captured image. In this case, the configuration of the display data analysis apparatus 1001 is also the same as that in FIG. 18. An internal configuration of the image analysis apparatus 304 is as shown in FIG. 26. The image analysis apparatus 304 at this time is configured by a marker recognition section 401 and an image recognition section 403. It is the marker recognition section 401 that actually detects/recognizes the corner markers 21 in FIG. 20 and the image recognition section 403 performs display/recognition based on the information acquired by the marker recognition section 401. The functions of the marker recognition section 401 and the image recognition section 403 are the same as those explained using FIG. 19, but it is also possible for the image recognition section 403 to identify the type of the measuring instrument 1 to which the corner markers 21 are attached using differences in the attaching positions of the corner markers 21 and differences in the number of the attached corner markers 21.

Figure 21:
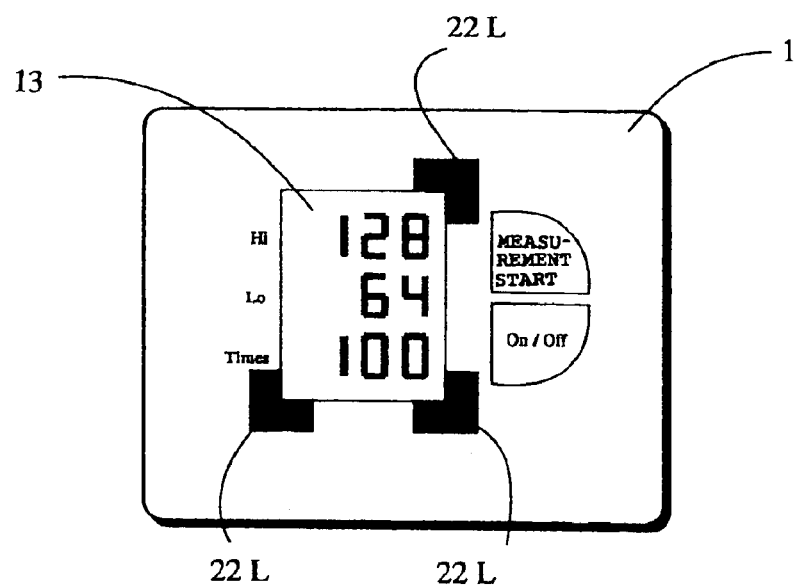
FIG. 21 is a configuration diagram of a measuring instrument with L markers attached.

Moreover, in FIG. 21 attaching L-type markers 22 makes detection of the measured data display screen 13 easier. In this case, the configuration of the display data analysis apparatus 1001 is also the same as that in FIG. 18. An internal configuration of the image analysis apparatus 304 is as shown in FIG. 26. The image analysis apparatus 304 at this time is configured by a marker recognition section 401 and an image recognition section 403. It is the marker recognition section 401 that actually detects/recognizes the L markers 22 in FIG. 21 and the image recognition section 403 performs display/recognition based on the information acquired by the marker recognition section 401.

Figure 22:
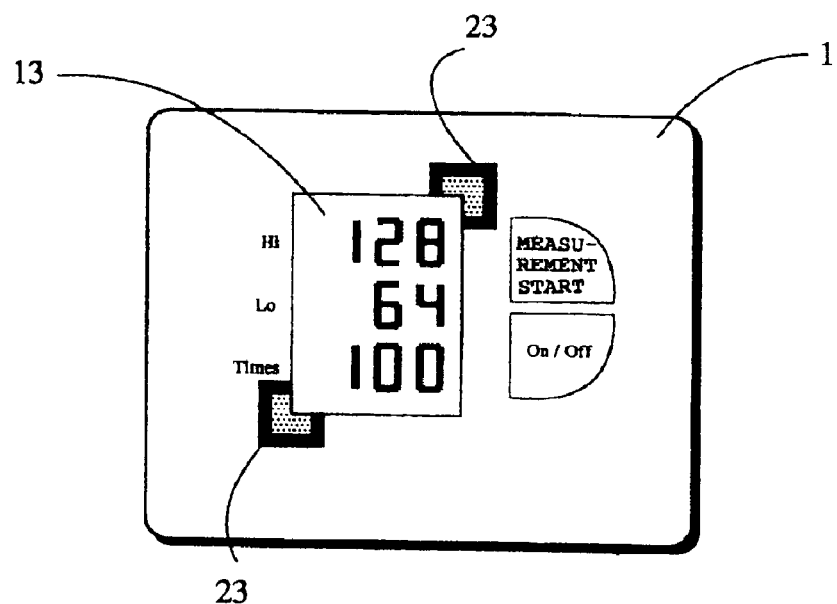
FIG. 22 is a configuration diagram of a measuring instrument with color markers attached.

Furthermore, in FIG. 22, attaching colormarkers 23 having a plurality of colors or a plurality of monochrome concentrations not only makes detection of the measured data display screen 13 easier but also improves the accuracy of detection of the markers themselves. In this case, the configuration of the display data analysis apparatus 1001 is also the same as that in FIG. 18. An internal configuration of the image analysis apparatus 304 is as shown in FIG. 26. The image analysis apparatus 304 at this time is configured by a marker recognition section 401 and an image recognition section 403. It is the marker recognition section 401 that actually detects/recognizes the color marker 23 in FIG. 22 and the image recognition section 403 performs display/recognition based on the information acquired by the marker recognition section 401.

Figure 23:
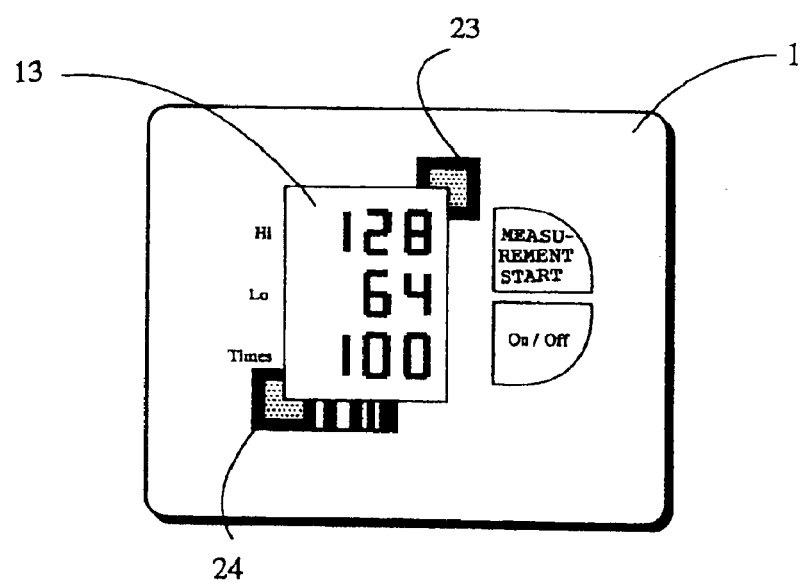
FIG. 23 is a configuration diagram of a measuring instrument with color markers and code markers attached.

In FIG. 23, a code marker 24 with a predetermined symbol added to detect a marker is further attached to the measuring instrument 1. This further improves the accuracy of marker detection. In this case, the configuration of the display data analysis apparatus 1001 is also the same as that in FIG. 18. An internal configuration of the image analysis apparatus 304 is as shown in FIG. 26. The image analysis apparatus 304 at this time is configured by a marker recognition section 401 and an image recognition section 403. It is the marker recognition section 401 that actually detects/recognizes the color marker 23 and code marker 24 in FIG. 23 and the image recognition section 403 performs display/recognition based on the information acquired by the marker recognition section 401.

Figure 27:
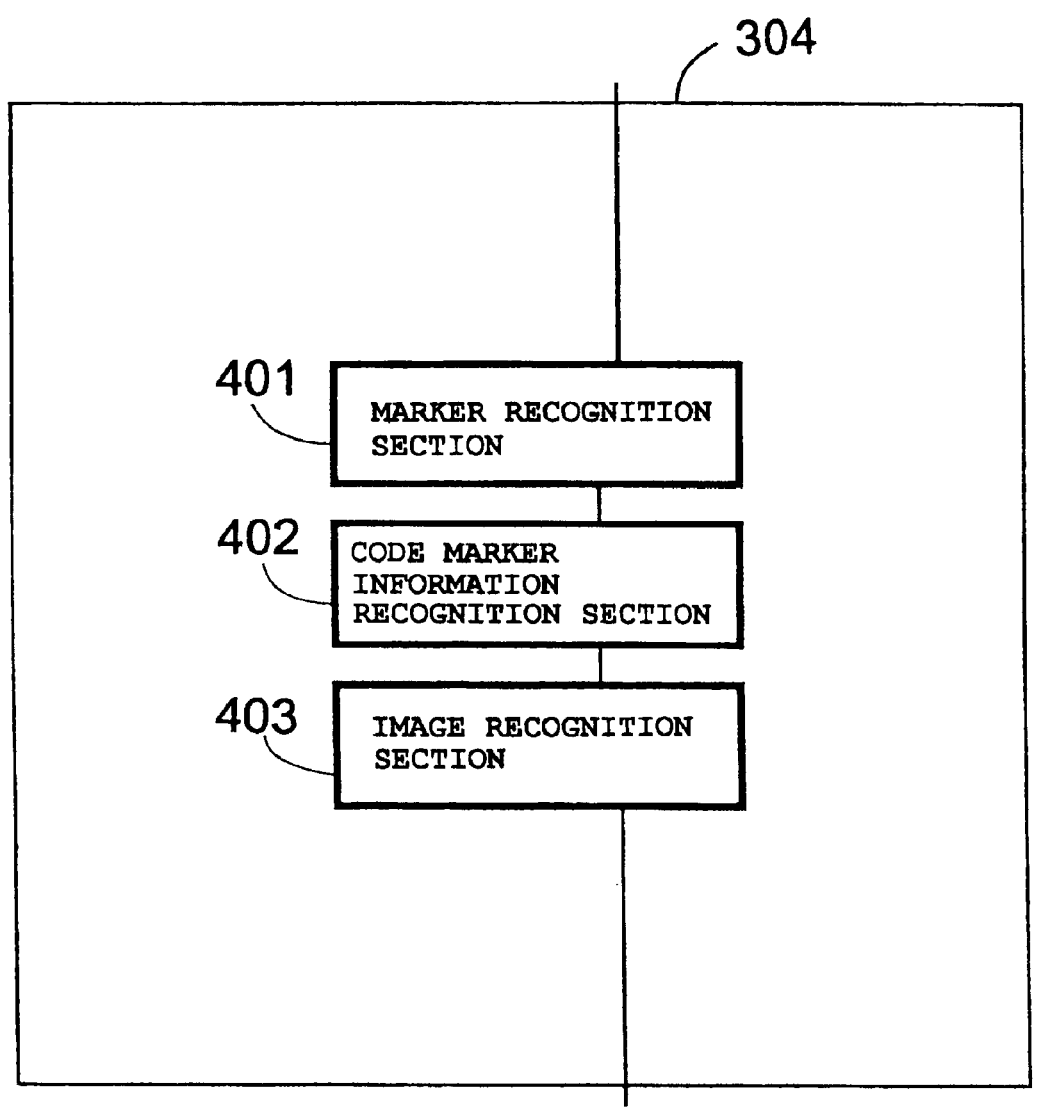
FIG. 27 is a schematic configuration diagram of an image analysis apparatus corresponding to a measuring instrument with code markers different from those in FIG. 26 attached.

The internal configuration of the image analysis apparatus 304 can also be as shown in FIG. 27 instead of FIG. 26. The image analysis apparatus 304 at this time is configured by the marker recognition section 401, code marker information recognition section 402 and image recognition section 403. It is the marker recognition section 401 that detects and recognizes the color marker 23 and code marker 24 in FIG. 23 and it is the code marker information recognition section 402 that detects and recognizes attribute information written in the code marker 24. The image recognition section 403 performs display/recognition based on the information obtained from the marker recognition section 401 and code marker information recognition section 402.

On the other hand, the attribute information written in the code marker 24 means, for example, information to identify the type of the measuring instrument 1 to which the code marker 24 is attached, the positions of numerical values, etc. displayed and the type of characters displayed in the measured data display screen 13 (numerical value only/alphanumeric only/alphabet only/kana only/, etc.), meanings expressed by each character string (maximum blood pressure, minimum blood pressure, heart rate, average body heat, etc. in that order from the top) or limit information of the character string type expressed by each character string (displays only 2 to 3-digit numerical value and "Err" or displays only numerical values such as 30.0 to 42.0, etc.).

Of course, the attribute information written in the code marker 24 can also be any combination of the items above and is not limited to the above information.

The embodiment above describes a case where the image analysis apparatus 304 detects the measured data display screen 13 of the measuring instrument 1 using the marker 20, corner marker 21, L marker 22, color marker 23 and code marker 24, but in the case where the measured data display screen 13 is a fixed display screen of LCD, etc. that displays a 7-segment number, etc. and the color and reflectivity of light of the measured data display screen 13 is different from the outside of the measured data display screen 13, the image analysis apparatus 304 can also detect the measured data display screen 13 using the difference of the color and reflectivity. Then, it is also possible to analyze and recognize numerical value data, etc. in the detected-measured data display screen 13. In this case, the detection auxiliary information is configured by information on the color and reflectivity of the measured data display screen 13 and the database indicating which color or reflectivity indicates the measured data display screen 13, etc.

Furthermore, the image analysis apparatus 304 can also detect the shape and color arrangement situation of the measuring instrument 1, identify the type of the measuring instrument 1 and the position of the measured data display screen 13 and detect the measured data display screen 13. In this case, the detection auxiliary information is configured by information on the shape and color arrangement situation of the measuring instrument 1 and the database indicating where the measured data display screen 13 is located with what shape and color arrangement situation.

The embodiment above does not describe how the image recognition section 403 inputs the analysis auxiliary information to identify the meaning, etc. of numerical values in the measured data display screen 13. An example of the image recognition section 403 inputting the analysis auxiliary information will be described below using FIG. 28.

Figure 28:
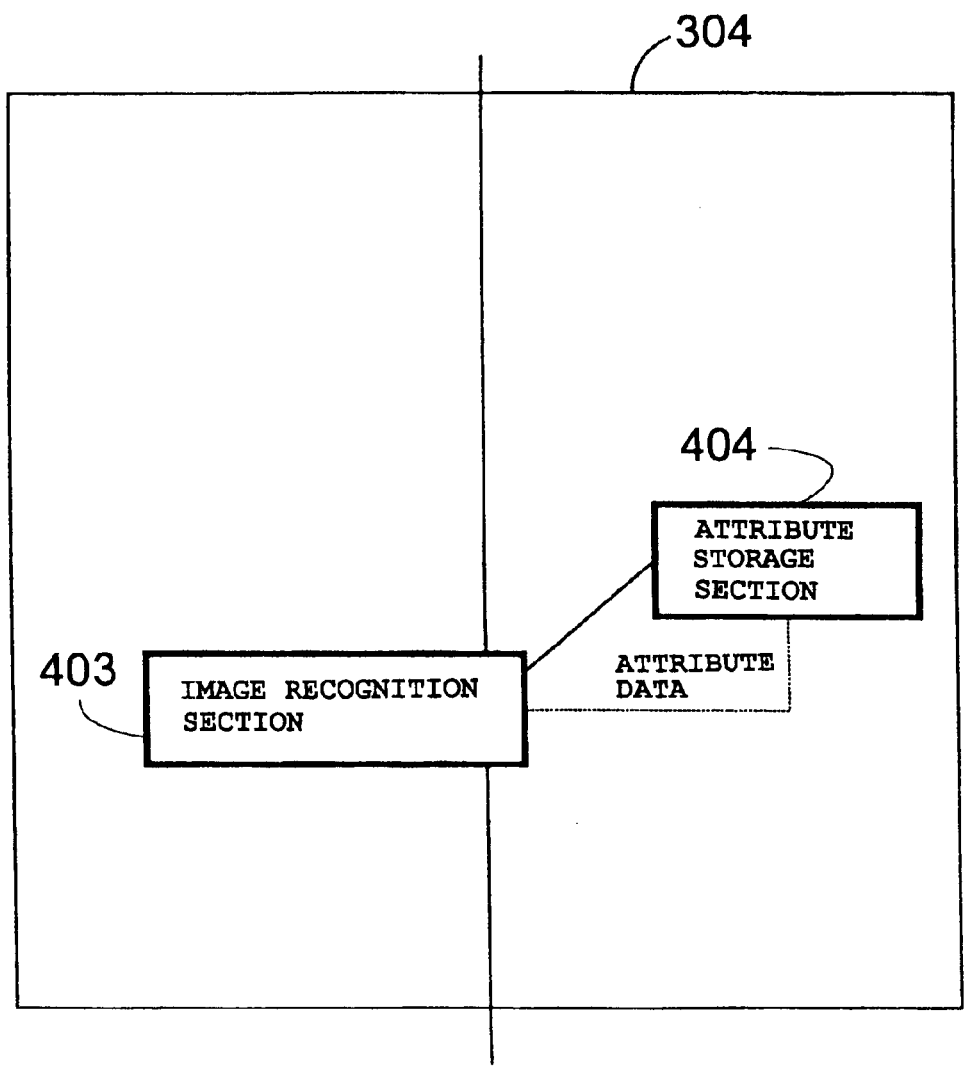
FIG. 28 is a schematic configuration diagram of the image analysis apparatus of the display data analysis apparatus in FIG. 18 different from FIG. 25.
Figure 29:
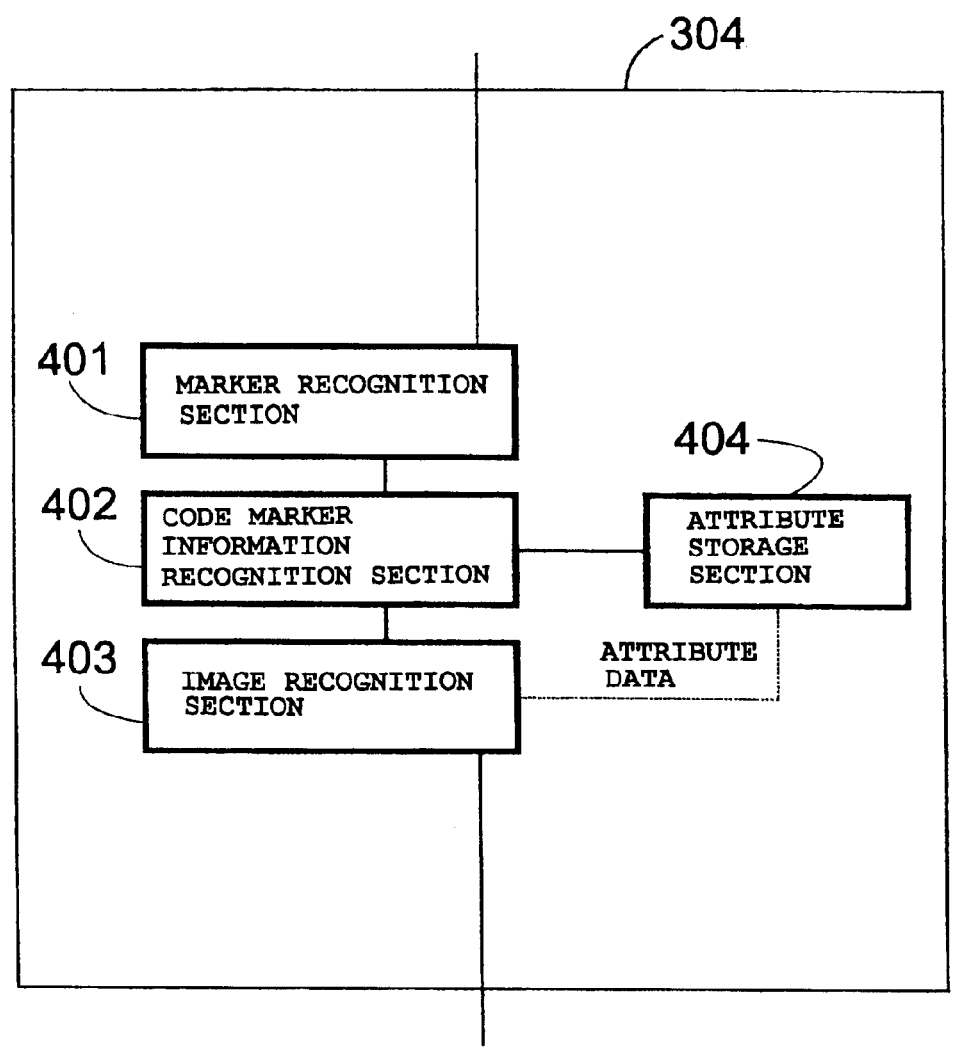
FIG. 29 is a schematic configuration diagram of the image analysis apparatus of the display data analysis apparatus in FIG. 24.

As shown in FIG. 28, the image analysis apparatus 304 is configured by the image recognition section 403 and attribute storage section 404, and the image recognition section 403 identifies the measuring instrument based on the image of the measuring instrument 1 input from the image input section 301 and based on the identification information acquires the analysis auxiliary information (attribute data) of the target measuring instrument from the attribute storage section 404. The attribute storage section 404 provides the attribute data corresponding to the measuring instrument information inquired from the image recognition section 403 for the image recognition section 403. The image recognition section 403 analyzes and recognizes the measured data display screen of the input image and data written inside based on the attribute data provided. Here, an example of the storage means according to claim 8 is the attribute storage section 404.

Figure 24:
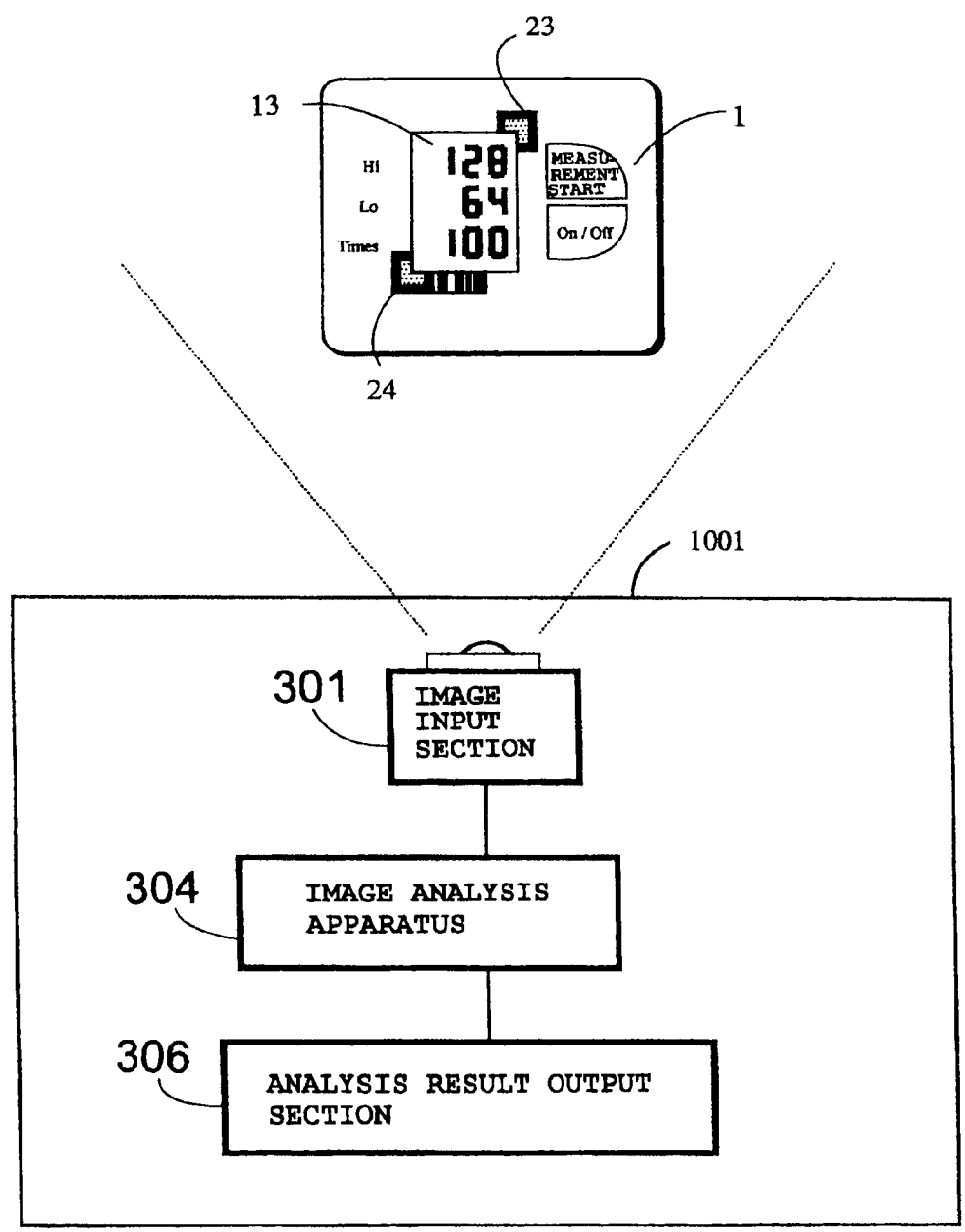
FIG. 24 is a schematic configuration diagram of a display data analysis apparatus that detects a measured data display screen of measuring instruments using color markers and code markers and analyzes the measured data.

Next, FIG. 24 shows a configuration of the display data analysis apparatus 1001 that detects the measured data display screen 13 of the measuring instrument 1 and analyzes the measured data using the color marker 23 and code marker 24. However, the type, shape or position, etc. of these markers attached to the measuring instrument 1 are not limited to this, but they are only shown as an example. An internal configuration of the image analysis apparatus 304 of the display data analysis apparatus 1001 is as shown in FIG. 12. The image analysis apparatus 304 at this time is configured by a marker recognition section 401, a code marker information recognition section 402, an image recognition section 403 and an attribute storage section 404.

It is the marker recognition section 401 that actually detects and recognizes the color marker 23 and code marker 24 in FIG. 24 and it is the code marker information recognition section 402 that detects and recognizes the attribute information written in the code marker 24. The code marker information recognition section 402 identifies the measuring instrument and acquires the attribute data of the target measuring instrument from the attribute storage section 404 based on the identification information. The attribute storage section 404 provides the attribute data corresponding to the measuring instrument information inquired from the code marker information recognition section 402 to the image recognition section 403. The image recognition section 403 analyzes and recognizes the measured data display screen 13 of the input image and the data written inside based on the attribute data provided.

Figure 31:
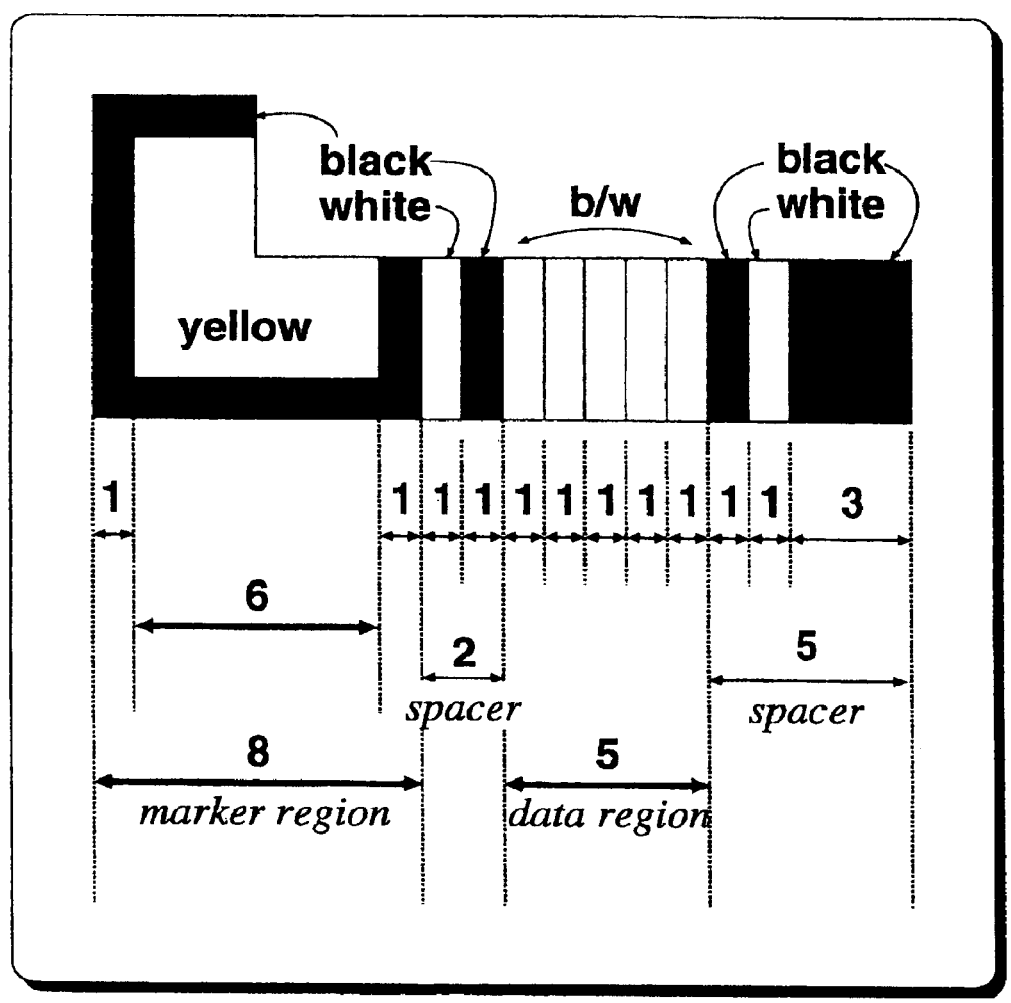
FIG. 31 is a configuration diagram of a code section of a code marker.

Here, FIG. 31 shows an example of the format of the information described in the code marker 24. This shows an example of a code marker that consists of a yellow and black marker sections and a black and white barcode-like information section based on an L-type marker. The sizes (numerical values) shown in FIG. 31 are all expressed in ratios. The data described is written with a white or black bar in the range of 5 bands of the data region.

The method of configuring the code marker 24 is naturally not limited to this, but any configuration method can be selected.

On the other hand, attribute data coded in some technique is written in the symbols of the code marker 24. For this coding method, a so-called barcode or QR code, etc., for example, can be used, but any method can also be used without being limited to this. Adding attribute data to symbols in this way can further improve the accuracy of marker detection. The configuration of the display data analysis apparatus 1001 in this case is also the same as that in FIG. 18. An internal configuration of the image analysis apparatus 304 is as shown in FIG. 27. The image analysis apparatus 304 at this time is configured by a marker recognition section 401, a code marker information recognition section 402 and an image recognition section 403. The code marker 24 with attribute data added is detected by the marker recognition section 401 and the attribute data is actually detected, recognized and decoded by the code marker information recognition section 402. The decoding means of the code marker information recognition section 402 corresponds to the previously coded means.

In this way, the code marker information recognition section 402 acquires the coded attribute data by analyzing, decoding and recognizing the captured image of a predetermined symbol in which this attribute data is written. The image recognition section 403 analyzes and recognizes the measured data display screen of the input image and the data written inside based on the acquired attribute data.

FIG. 24 shows an example in which one code marker 24 and one color marker 23 are attached to the measuring instrument 1, but the type and number of markers are not limited to this.

Moreover, the color marker 23 in FIG. 22 and FIG. 24 are of L-type, but it is not limited to L-type. It goes without saying that any figure or any number of colors or any configuration pattern can also be used. FIG. 30 shows examples of a shape/configuration pattern of the color marker 23. Likewise, the code marker 24 in FIG. 24 contains an L-type structure, but its shape, color used, number of colors and configuration pattern, etc. are arbitrary.

The explanations so far describe cases where an appropriate number of markers are used. Markers can be naturally attached to all the four corners of the measured data display screen 13 or only one can be attached or they can be configured with an arbitrary number and positions. Moreover, it goes without saying that the format of data written in the code marker 24 can be configured arbitrarily. Here, regarding the shape of markers, a rectangular or L-type marker is used, but the shape is not necessarily limited to this, either.

Next, the above described measuring instrument 1 is not limited to a sphygmomanometer, but can also be a vital sensor that measures other living body information. In that case, the display data analysis apparatus 1001 analyzes the display data of this vital sensor. This makes it possible to use a existing vital sensor and input data to a host machine without dedicated wired or wireless IF (RS232C or IrDA, etc.), which is a conventional input IF, or numeric keypad or keyboard to control various measured values obtained in a hospital or home, etc. in a centralized control. Moreover, the measuring instrument 1 is not limited to a vital sensor. Even in such case like that, the display data analysis apparatus 1001 can be also used to analyze the display data of the measuring instrument 1.

Moreover, the above described host machine can also be a vital sign box. Here, the vital sign box collects and controls the output from the vital sensor and communicates and corresponds with a doctor and can function as a communication terminal as well as a host machine. By directly outputting measured data of the vital sensor to this vital sign box, the user can use the vital sensor on hand as is and can input data to the vital sign box without any input means like a numeric keypad or keyboard.

Figure 32:
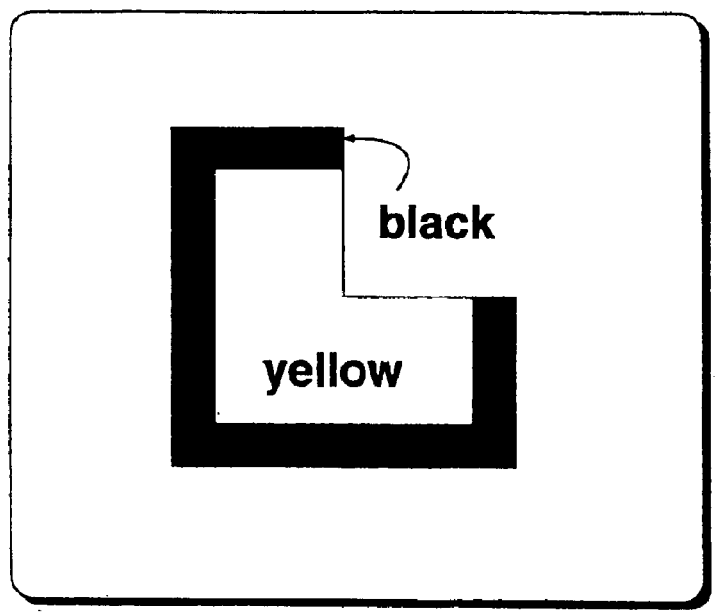
FIG. 32 is a configuration diagram of a marker.

For all the embodiments so far, any method of detecting various markers in the marker recognition section 401 can be used according to the shape and tone of color, etc. of the markers. For example, in the case of an yellow and black L-type marker shown in FIG. 32, the marker recognition section 401 operates in the following sequence:

1) Searches the yellow area.
2) Checks whether the yellow area has an area equal to or greater than a predetermined size.
3) Checks whether a black area exists around the yellow area.
4) Checks whether the detected shape is similar to an L-type shape.

However, these are only examples.

Likewise, the code marker information recognition section 402 operates in the following sequence, for example:

1) Binary-codes the code information area.
2) Reads code information from the binary black/white information.

These are only examples and it goes without saying that any method can be used to analyze data by the code marker information recognition section 402.

Furthermore, the image recognition section 403 operates in the following sequence, for example:

1) Identifies a data display area (uses marker information if any or also uses code marker information if any).
2) Identifies the data position in the data display area (uses attribute data if any).
3) Recognizes respective data in the data display area (uses arbitrary processing such as pattern matching).

These are only examples and it goes without saying that any other method can also be used.

Figure 33:
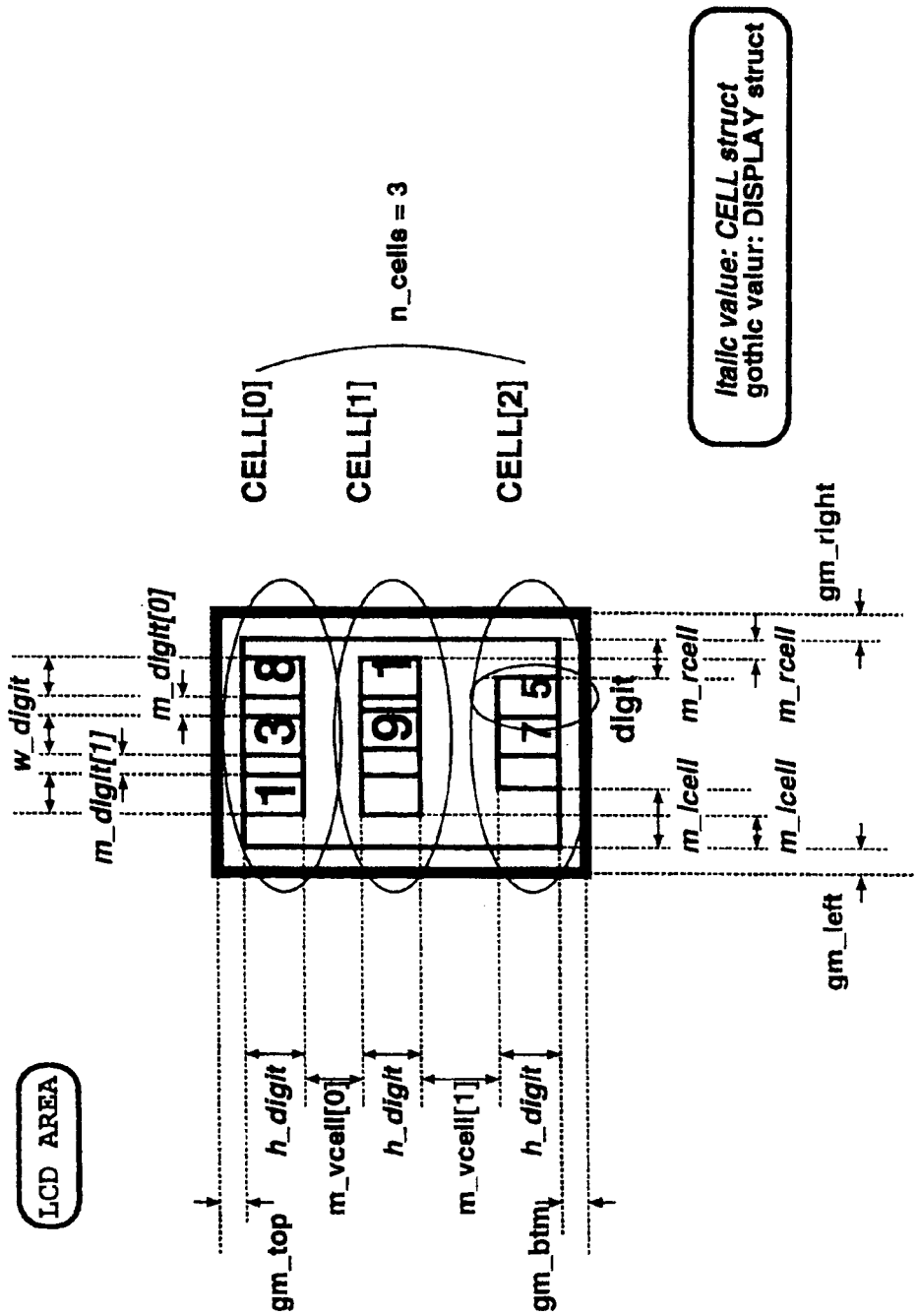
FIG. 33 is a drawing to explain attribute data.

Moreover, the attribute data stored in the attribute storage section 404 are properties of measured data display screens of various measuring instruments and their information can be written as shown in FIG. 33, for example. Of course, the written content and format of the attribute data can be configured arbitrarily.

The following is an explanation of FIG. 33.

FIG. 33 shows an example of a data display screen of a sphygmomanometer and an example of its property setting. The data display screen shows three numerical values 138, 91 and 75 in that order from the top (values indicating a maximum blood pressure, minimum blood pressure, heart rate, in that order).

As a property to recognize these values, a number of constants are set for the LCD section (data display section) In the example, a number of constants are defined regarding the property for each LCD section as a DISPLAY structure by imitating a C-language program.

```
typedef struct{
unsigned char n_digit;// number of digits of each cell, max.
5 digits
unsigned char n_idigit;// number of digits integer part of
each cell
short max_value;// maximum value
    (however, suppose all digits are integers. ex., 34.5
    → 345)
short min_value;// minimum value
    (however, suppose all digits are integers. ex., 34.5
    → 345)
unsigned char h_digit;// height of digits in cell
    (suppose overall height of LCD section is 100)
unsigned char w_digit;// width of digits in cell
    (suppose overall width of LCD section is 100)
unsigned char f_digit;// "0" if information included in cell
is only 7-seg data
// takes a value other than "0", otherwise
unsigned char m_digit[4];// margin between each digit
    (suppose overall width of LCD section is 100)
//digit[0] (equivalenttofirstdigit),cell[1] (seconddigit)
margin is m_digit[0].
unsigned char m_rcell;// right margin of each cell
unsigned char m_lcell;// left margin of each cell
} CELL;
// property of every LCD section
typedef struct{
char hinban[20];// product number. National DM-B3, etc.
int censor_type;// defines clinic
thermometer/sphygmomanometer, etc.
int display_type;// indicates meaning of LCD section
information.
    (maximum blood pressure from top . . . etc.)
unsigned char gm_top;// global margin (from the top edge of
the display)
unsigned char gm_bottom; // global margin (from the bottom edge
of the display)
unsigned char gm_right;// global margin (from the right edge
of the display)
unsigned char gm_left;// global margin (from the left edge
of the display)
unsigned char n_cells;// number of cells included in LCD
section (= number of data pieces. 3 in this case)
unsigned char m_vcell[4];// margin in vertical direction
between cells.
    m_vcell[0] between cell[0],[1]
CELL cell[5];// individual information of each cell
} DISPLAY;
```

When the measuring instrument is identified, the DISPLAY structure corresponding to the measuring instrument is loaded from the attribute storage section 404. The DISPLAY structure includes hinban[20] that indicates the product number, censor_type that indicates the type of the measuring instrument (thermometer/sphygmomanometer/ blood sugar meter, etc.), display type that indicates the meaning of the display content of the display section (maximum blood pressure, minimum blood pressure, heart rate, etc. in that order from the top), 4 constants starting with gm_that indicates each numerical value and margin from the peripheral section of the display section, n_cells that indicates the number of character string (numerical value) data pieces displayed on the display section, cell[5] that contains property belonging to each character string (numerical value) data, m_vcell[4] that indicates each character string (numerical value) data, that is, margin in vertical direction between cells, etc.

FIG. 33 defines the numerical values as cell[0], cell[1], cell[2] in that order from the top. The sum total of cells varies depending on the number of numerical values appearing on the data display screen of each measuring instrument. In the example of this sphygmomanometer, it is three; maximum blood pressure, minimum blood pressure, heart rate. That is, in the example, n_cell s=3.

It is the cell structure that maintains a property about each for each cell. The CELL structure includes n_digit that indicates the number of the digit cell of each, n_idigit that indicates the integer part of each cell, max-value that indicates a maximum value, min_value that indicates a minimum value, h_digit and w-digit that indicate the height and width of the digit in each cell, f_digit that indicates whether the digit in each cell indicates data other than a numerical value or not (whether it indicates a 7-seg data other than a numerical value in the case of LCD display, that is, a 7-seg character in general), m_digit[4] that indicates a margin between digits in each cell (in this case, maximum 5 digits, and so there are 4 margins) and m_rcell and m_lcell that indicate the right and left margins of each cell, etc.

FIG. 33 shows what kind of width, margin, digit or cell these properties express respectively. In the figure, the constants expressed in italics are properties that belong to the CELL structure and those in gothic are properties that belong to the DISPLAY structure.

Setting such properties can extract and recognize data of the display section more easily and more accurately.

Of course, the method of configuring definitions and properties of a structure is not limited to this, but these can be configured arbitrarily.

As shown above, the display data analysis apparatus 1001 of this embodiment implements what conventionally requires a measuring instrument equipped with dedicated interface equipment using the existing measuring instrument as is and makes it possible to perform data communication with a host machine. The invention concerning a series of markers also improves the accuracy of recognition of the display section a great deal to the extent of practical use.

Moreover, in the case of a vital sensor box, etc. targeted especially at senior citizens, many users are unfamiliar with machines such as a PC, but the display data analysis apparatus 1001 of this embodiment provides an extremely simple input means, which brings a great effect in the practical aspect.

The present invention is a medium that carries a program and/or data to make a computer execute all or some of functions of all or some of the above described means of the present invention and is a medium that can be read by a computer and a medium in which the read program and/or data can function together with the computer to execute the above described functions.

Furthermore, the present invention is an information aggregate, which is a program and/or data for a computer to execute all or some of functions (operations) of all or some of the above described means (steps) of the present invention and is an information aggregate that can be read by a computer and an information aggregate in which the read program and/or data can function together with the computer to execute the above described functions (operations).

Here, the "data" includes a data structure, data format and data type, etc.

The "medium" includes a recording medium such as ROM, a transmission medium such as the Internet and a transmission medium such as optical, radio wave and sound wave.

The "carried medium" includes, for example, a recording medium that records a program and/or data and a transmission medium that transmits a program and/or data, etc.

"Being processable by a computer" means that can be read by a computer in the case of a recording medium such as ROM or that a program and/or data that is a transmission target can be handled by a computer as a result of transmission in the case of a transmission medium.

An "information aggregate" includes, for example, software such as a program and/or data.

As explained above, the configuration of the present invention can be implemented by software as well as hardware.

As described above, the invention disclosed by this application needs no special hardware or software for communications between measuring instruments and the main unit, making it possible to implement a data input apparatus at low cost.

Furthermore, the present invention needs no special hardware for measuring instruments, allowing measuring instruments generally available on the market and provided by vendors to be used in the present invention.

Moreover, "not performing communications" means that no such work as standardization of a communication protocol is required, making it possible to reduce the number of man hours for development of a data input apparatus.

Furthermore, the present invention is always applicable to latest measuring instruments through maintenance of database for recognition of the measuring instruments, providing an easy way of additions/changes of the measuring instruments, preventing the data input apparatus from being obsolete.

Furthermore, the present invention can provide a display data analysis apparatus that allows measured data measured and displayed by a measuring instrument not equipped with an interface corresponding to a processing apparatus to be output to the above processing apparatus without using the above interface or requiring manual input.

What is claimed is:

1. A display data analysis apparatus that analyzes measured data measured and displayed by a predetermined measuring apparatus and outputs the analysis result to a predetermined processing apparatus, comprising:

an image acquiring unit acquiring an image of data by directly inputting the image displayed on a data display section of a measuring instrument;

a detecting unit detecting the measured data displayed by said measuring apparatus in the image picked up by said image acquiring unit using detection auxiliary information to detect the measured data displayed by said measuring apparatus;

an analyzing unit analyzing the measured data in the image picked up by said image acquiring unit using analysis auxiliary information to analyze the measured data displayed by said measuring apparatus in the case where said measured data is detected by said detecting unit; and an outputting unit outputting the analysis result analyzed by said analyzing unit;

wherein the image acquiring unit includes a camera for focusing on the display of the measuring instrument and acquiring the image displayed thereon, said detection auxiliary information and/or said analysis auxiliary information includes indices attached to said measuring apparatus and database concerning the indices, and said indices are of L-type or rotated L-type.

2. A display data analysis apparatus that analyzes measured data measured and displayed by a predetermined measuring apparatus and outputs the analysis result to a predetermined processing apparatus, comprising:

an image acquiring unit acquiring an image of data by directly inputting the image displayed on a data display section of a measuring instrument;

a detecting unit detecting the measured data displayed by said measuring apparatus in the image picked up by said image acquiring unit using detection auxiliary information to detect the measured data displayed by said measuring apparatus;

an analyzing unit analyzing the measured data in the image picked up by said image acquiring unit using analysis auxiliary information to analyze the measured data displayed by said measuring apparatus in the case where said measured data is detected by said detecting unit; and an outputting unit outputting the analysis result analyzed by said analyzing unit;

wherein the image acquiring unit includes a camera for focusing on the display of the measuring instrument and acquiring the image displayed thereon, said detection auxiliary information and/or said analysis auxiliary information includes indices attached to said measuring apparatus and database concerning the indices, and said indices have a plurality of colors or a plurality of concentrations in the case of monochrome.

3. A display data analysis apparatus that analyzes measured data measured and displayed by a predetermined measuring apparatus and outputs the analysis result to a predetermined processing apparatus, comprising:

an image acquiring unit acquiring an image of data by directly inputting the image displayed on a data display section of a measuring instrument;

a detecting unit detecting the measured data displayed by said measuring apparatus in the image picked up by said image acquiring unit using detection auxiliary information to detect the measured data displayed by said measuring apparatus;

an analyzing unit analyzing the measured data in the image picked up by said image acquiring unit using analysis auxiliary information to analyze the measured data displayed by said measuring apparatus in the case where said measured data is detected by said detecting unit; and an outputting unit outputting the analysis result analyzed by said analyzing unit;

wherein the image acquiring unit includes a camera for focusing on the display of the measuring instrument and acquiring the image displayed thereon, and said detection auxiliary information includes color/reflectivity information on colors and/or reflectivity of the display section of the measured data of said measuring apparatus and database concerning the colors/reflectivity information.

4. A display data analysis apparatus that analyzes measured data measured and displayed by a predetermined measuring apparatus and outputs the analysis result to a predetermined processing apparatus, comprising:

an image acquiring unit acquiring an image of data by directly inputting the image displayed on a data display section of a measuring instrument;

a detecting unit detecting the measured data displayed by said measuring apparatus in the image picked up by said image acquiring unit using detection auxiliary information to detect the measured data displayed by said measuring apparatus;

an analyzing unit analyzing the measured data in the image picked up by said image acquiring unit using analysis auxiliary information to analyze the measured data displayed by said measuring apparatus in the case where said measured data is detected by said detecting unit; and an outputting unit outputting the analysis result analyzed by said analyzing unit;

wherein the image acquiring unit includes a camera for focusing on the display of the measuring instrument and acquiring the image displayed thereon, and said detection auxiliary information includes shape/color arrangement information on the shape and/or color arrangement situation of said measuring apparatus and database concerning the shape/color arrangement information.

5. A display data analysis apparatus that analyzes measured data measured and displayed by a predetermined measuring apparatus and outputs the analysis result to a predetermined processing apparatus, comprising:

an image acquiring unit acquiring an image of data by directly inputting the image displayed on a data display section of a measuring instrument;

a detecting unit detecting the measured data displayed by said measuring apparatus in the image picked up by said image acquiring unit using detection auxiliary information to detect the measured data displayed by said measuring apparatus;

an analyzing unit analyzing the measured data in the image picked up by said image acquiring unit using analysis auxiliary information to analyze the measured data displayed by said measuring apparatus in the case where said measured data is detected by said detecting unit; and an outputting unit outputting the analysis result analyzed by said analyzing unit;

wherein the image acquiring unit includes a camera for focusing on the display of the measuring instrument and acquiring the image displayed thereon, and said measuring apparatus is a vital sensor that measures living body information, said measured data is display data of the vital sensor and said processing apparatus is a vital sign box.

6. In a monitoring system including a plurality of differing measuring devices, each measuring a parameter of an object and displaying a parameter value on a display, a method of recording the parameter value from each measuring device comprising the steps of:

(a) identifying each respective measuring device;

(b) capturing a display of the measuring device identified in step (a) as an image to extract a parameter value displayed on the display; and (c) inputting the parameter value extracted in step (b) to a data collection terminal;

wherein the step of capturing the display includes focusing on the display of the measuring device, using a camera, to extract the parameter value displayed thereon, and step (a) includes forming at least two markers on the display, and scanning the markers to (i) identify the respective measuring device and (ii) identify the parameter value between the two markers.

7. In a health monitoring system including a plurality of differing measuring devices, each measuring a health parameter of a patient and displaying a health parameter value on a display, a method of recording the health parameter value from each measuring device comprising the steps of:

(a) identifying each respective measuring device;

(b) capturing a display of the measuring device identified in step (a) as an image to extract a health parameter value displayed on the display; and (c) inputting the health parameter value extracted in step (b) to a data collection terminal;

wherein the step of capturing the display includes focusing on the display of the measuring device, using a camera, to extract the parameter value displayed thereon, and step (a) includes forming at least two markers on the display, and scanning the markers to (i) identify the respective measuring device and (ii) identify the parameter value between the two markers.

8. A display data analysis apparatus that analyzes measured data measured and displayed by a predetermined measuring apparatus and outputs the analysis result to a predetermined processing apparatus, comprising:

an imaging unit picking up an image;

a detecting unit detecting the measured data displayed by said measuring apparatus in the image picked up by said imaging unit using detection auxiliary information to detect the measured data displayed by said measuring apparatus;

an analyzing unit analyzing the measured data in the image picked up by said imaging unit using analysis auxiliary information to analyze the measured data displayed by said measuring apparatus in the case where said measured data is detected by said detecting unit; and an outputting unit outputting the analysis result analyzed by said analyzing unit, wherein the measuring apparatus includes at least two markers, and the detecting unit is configured to scan the image of the markers to (a) identify the measuring apparatus and (b) identify the measured data displayed between the two markers.

* * * * *